United States Patent [19]

Galy

[11] Patent Number: 6,015,554
[45] Date of Patent: *Jan. 18, 2000

[54] METHOD OF RECONSTITUTING HUMAN LYMPHOID AND DENDRITIC CELLS

[75] Inventor: Anne H. M. Galy, Palo Alto, Calif.

[73] Assignee: SyStemix, Inc., Palo Alto, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/487,083

[22] Filed: Jun. 7, 1995

Related U.S. Application Data

[63] Continuation of application No. 08/464,678, filed as application No. PCT/US95/03038, Mar. 9, 1995, abandoned, which is a continuation-in-part of application No. 08/260,185, Jun. 15, 1994, abandoned.

[51] Int. Cl.$^7$ .......................... A61K 35/26; A61K 35/28; C12N 5/08
[52] U.S. Cl. .......................... 424/93.7; 424/577; 435/7.2; 435/372
[58] Field of Search .......................... 435/2, 7.2, 7.24, 435/240.2, 372; 424/93.7, 529, 577

[56] References Cited

U.S. PATENT DOCUMENTS

| | | |
|---|---|---|
| 4,714,680 | 12/1987 | Civin . |
| 5,061,620 | 10/1991 | Tsukamoto et al. . |
| 5,147,784 | 9/1992 | Peault . |
| 5,359,046 | 10/1994 | Capon et al. . |
| 5,409,825 | 4/1995 | Hoffman et al. . |
| 5,605,829 | 2/1997 | McGlave et al. . |

FOREIGN PATENT DOCUMENTS

| | | |
|---|---|---|
| 0322240 | 6/1989 | European Pat. Off. . |
| WO 91/16451 | 10/1991 | WIPO . |
| WO 93/08268 | 4/1993 | WIPO . |
| WO 94/02016 | 2/1994 | WIPO . |
| WO 95/06409 | 3/1995 | WIPO . |

OTHER PUBLICATIONS

Bloom "A Perspective of AIDS Vaccines" *Science* (1996) 272:1888–1890.

Mayani et al. "Cytokine–Induced Selective Expansion and Maturation of Erythroid Versus Myeloid Progenitors from Purified Cord Blood Precursor Cells" *Blood* (1993) 81(12):3252–3258.

Mayani et al. "Characterization of Functionally distinct Subpopulations of CD34$^+$ Cord Blood Cells in Serum–Free Long–Term Cultures Supplemented with Hematopoietic Cytokines" *Blood* (1993) 82(9):2664–2672.

Schmidt et al. "Expression of CD34 on human B cell precursors" *Clin. Exp. Immunol.* (1991) 85:168–173.

Bender et al., "Phenotypic analysis and characterization of CD34$^+$ cells from normal human bone marrow, cord blood, peripheral blood and mobilized peripheral blood from patients undergoing autologous stem cell transplantation" *Clinical Immunology and Immunopathology* (1994) 70:10–18.

Galy et al., "Human T, B, Natural Killer and Dendritic Cells arise from a common bone marrow progenitor cell subset" *Immunity* (1995) 3:459–473.

van Noesel et al., "Architecture of the human B–cell antigen receptors" *Blood* (1993) 82:363–373.

Godfrey et al., "Control points in early T–cell development" *Immunol. Today* (1993) 14:547–553.

Uckun, "Regulation of human B–cell ontogeny" *Blood* (1990) 76:1908–1923.

Li et al., "The regulated expression of B lineage associated genes during B cell differentiation in bone marrow and fetal liver" *J. Exp. Med.* (1993) 178:951–960.

LeBien et al., "The common acute lymphoblastic leukemia antigen (CD10)—emancipation from a functional enigma" *Blood* (1989) 73:625–635.

Galy et al., "Percursors of CD3$^+$CD4$^+$CD8$^+$ cells in the human thymus are defined by expression of CD34. Delineation of early events in human thymic development" *J. Exp. Med.* (1993) 178:391–401.

Terstappen et al., "Flow cytometric assessment of human T–cell differentiation in thymus and bone marrow" *Blood* (1992) 79:666–677.

Sánchez et al., "Human natural killer cell committed thymocytes and their relation to the T cell lineage" *J. Exp. Med.* (1993) 178:1857–1866.

Terstappen et al., "Sequential generations of hematopoietic colonies derived from single nonlineage–committed CD34$^+$CD38$^-$ progenitor cells" *Blood* (1991) 77:1218–1227.

Le Douarin et al., "Origin and renewal of lymphocytes in avian embryo thymuses studied in interspecific combinations" *Nature New Biol.* (1973) 246:25–27.

Scollay et al., "Dynamics of early T cells: Prothymocyte migration and proliferation in the adult mouse thymus" *Immunol. Rev.* (1986) 91:129–157.

McCune et al., "The SCID–hu mouse: Murine model for the analysis of human hematolymphoid differentiation and function" *Science* (1988) 241:1632–1639.

Péault et al., "Lymphoid reconstitution of the human fetal thymus in SCID mice with CD34$^+$ precursor cells" *J. Exp. Med.* (1991) 174:1283–1286.

(List continued on next page.)

*Primary Examiner*—Christina Y. Chan
*Assistant Examiner*—Evelyn Rabin
*Attorney, Agent, or Firm*—Melissa A. Shaw

[57] ABSTRACT

The invention relates to methods of enriching for hematopoietic cell populations enriched in myeloid and/or lymphoid progenitor cells based on cell specific markers. The methods also provide an enriched population of prethymic lymphoid-committed progenitor population lacking long-term hematopoietic reconstitution potential. Compositions enriched for the cells and populations of cells obtained therefrom are also provided by the invention. Methods of use of the cells are also included. Methods of genetically modifying the cells are provided as are cells obtained thereby.

6 Claims, 24 Drawing Sheets

OTHER PUBLICATIONS

Bárcena et al., "Phenotypic and functional analysis of T–cell precursors in the human fetal liver and thymus: CD7 expression in the early stages of T– and myeloid–cell development" *Blood* (1993) 82:3401–3414.

Baum et al., "Isolation of a candidate human hematopoietic stem–cell population" *Proc. Natl. Acad. Sci. USA* (1992) 89:2804–2808.

Galy et al., "Generation of T cells from cytokine–mobilized peripheral blood and adult bone marrow CD34+ cells" *Blood* (1994) 84:104–110.

Srour et al., "Persistence of human multilineage, self–renewing lymphohematopoietic stem cells in chimeric sheep" *Blood* (1993) 82:3333–3342.

Landsdorp et al., "Long–term erythropoiesis from constant numbers of CD34+ cells in serum–free cultures initiated with highly purified progenitor cells from human bone marrow" *J. Exp. Med.* (1992) 175:1501–1509.

Srour et al., "Human CD34+ HLA–DR bone marrow cells contain progenitor cells capable of self–renewal, multilineage differentiation, and long–term in vitro hematopoiesis" *Blood Cells* (1991) 17:287–295.

Craig et al., "Expression of Thy–1 on human hematopoietic progenitor cells" *J. Exp. Med.* (1993) 177:1331–1342.

Udomsakdi et al., "Separation of functionally distinct subpopulations of primitive human hematopoietic cells using Rhodamine–123" *Exp. Hemamtol.* (1991) 19:338–342.

Lansdorp et al., "Selective expression of CD45 isoforms on functional subpopulations of CD34+ hemopoietic cells from human bone marrow" *J. Exp. Med.* (1990) 172:363–366.

Thomas, "The leukocyte common antigen family" *Ann. Rev. Immunol.* (1989) 7:339–369.

Sanders et al., "Human naive and memory T cells: Reinterpretation of helper–inducer and suppressor–inducer subsets" *Immunol. Today* (1988) 9:195–199.

Deans et al., "Prolonged expression of high molecular mass CD45RA isoform during the differentiation of human progenitor thymocytes to CD3+ cells in vitro" *J. Immunol.* (1991) 147:4060–4068.

Caux et al., "Activation of human dendritic cells through CD40 cross–linking" *J. Exp. Med.* (1994) 180:1263–1272.

Steinman, "The dendritic cell system and its role in immunogenicity" *Ann. Rev. Immunol.* (1991) 9:271–296.

Macatonia et al., "Dendritic cells and macrophages are required for Th1 development of CD4+ T cells from αβ TCR transgenic mice: IL–12 substitution for macrophages to stimulate IFN-$\gamma$ production is IFN-$\gamma$–dependent" *International Immunol.* (1993) 5:1119–1128.

Kampinga et al., "Differences in turnover between thymic medullary dendritic cells and a subset of cortical macrophages" *J. Immunol.* (1990) 145:1659–1663.

Ardavin et al., "Thymic dendritic cells and T cells develop simultaneously in the thymus from a common precursor population" *Nature* (1993) 362:761–763.

Winkel et al., "CD4 and CD8 expression by human and mouse thymic dendritic cells" *Immunol. Lett.* (1994) 40:93–99.

Miller et al., "Generation of helper–free and amphotropic retroviruses that transduce a dominant–acting, methotrexate–resistant dihydrofolate reductase gene" *Mol. Cell. Biol.* (1985) 5:431–437.

Miller et al., "Redesign of retrovirus packaging cell lines to avoid recombination leading to helper virus production" *Mol. Cell. Biol.* (1986) 6:2895–2902.

Danos et al., "Safe and efficient generation of recombinant retroviruses with amphotropic and ecotropic host ranges" *Proc. Natl. Acad. Sci. USA* (1988) 85:6460–6464.

Bregni et al., "Human peripheral blood hematopoietic progenitors are optimal targets of retroviral–mediated gene transfer" *Blood* (1992) 80:1418–1422.

Xu et al., "Correction of the enzyme deficiency in hematopoietic cells of Gaucher patients using a clinically acceptable retroviral supernatant transduction protocol" *Exp. Hematol.* (1994) 22:223–230.

Hughes et al., "Retroviral gene transfer to primitive normal and leukemic hematopoietic cells using clinically applicable procedures" *J. Clin. Invest.* (1992) 89:1817–1824.

Heusel et al., "Cytotoxic lymphocytes require granzyme B for the rapid induction of DNA fragmentation and apoptosis in allogeneic target cells" *Cell* (1994) 76:977–987.

Kuwana et al., "Expression of chimeric receptor composed of immunoglobulin–derived V regions and T–cell receptor–derived C regions" *Biochem. Biophys. Res. Comm.* (1987) 149:960–968.

Gross et al., "Generation of effector T Cells expressing chimeric T cell receptor with antibody type–specificity" *Trans. Proc.* (1989) 21:127–130.

Becker et al., "Expression of a hybrid immunoglobulin–T cell receptor protein in transgenic mice" *Cell* (1989) 58:911–921.

Gross et al., "Expression of immunoglobulin–T–cell receptor chimeric molecules as functional receptors with antibody–type specificity" *Proc. Natl. Acad. Sci. USA* (1989) 86:10024–10028.

Goverman et al., "Chimeric immunoglobulin–T cell receptor proteins form functional receptors: Implications for T cell receptor complex formation and activation" *Cell* (1990) 60:929–939.

Eshlar et al., "Specific activation and targeting of cytotoxic lymphocytes through chimeric single chains consisting of antibody–binding domains and the $\gamma$ or $\zeta$ subunits of the immunoglobulin and T–cell receptors" *Proc. Natl. Acad. Sci. USA* (1993). 90:720–724.

Hwu et al., "Lysis of ovarian cancer cells by human lymphocytes redirected with a chimeric gene composed of an antibody variable region and the Fc receptor $\gamma$ chain" *J. Exp. Med.* (1993) 178:361–366.

Sambrook et al., eds., *Molecular Cloning, A Laboratory Manual* (1989) Cold Spring Harbor Laboratory Press, New York. The title page and table of contents are enclosed herewith.

Schwinzer, "N7 cluster report: CD45/CD45R" *Leukocyte Typing IV. White Cell Differentiation Antigens,* Knapp et al., eds., (1989) Oxford University Press, New York, pp. 628–634.

Gunji et al., "Human primitive hematopoietic progenitor cells are more enriched in KIT$^{low}$ cells than in KIT$^{high}$ cells" *Blood* (1993) 82:3283–3289.

Mayani et al., "Thy–1 expression is linked to functional properties of primitive hematopoietic progenitor cells from human unbilical cord blood" *Blood* (1994) 83:2410–2417.

Kyoizumi et al., "Implantation and maintenance of functional human bone marrow in SCID–hu mice" *Blood* (1992) 79:1704–1711.

DiGiusto et al., "Human fetal bone marrow early progenitors to T, B, and myeloid cells are found exclusively in the population expressing high levels of CD34" *Blood* (1994) 84:421–432.

Murray et al., "The genes for leukemia inhibitory factor and interleukin–6 are expressed in mouse blastocysts prior to the onset of hemopoiesis" *Mol. Cell. Biol.* (1990) 10:4953–4956.

Miller et al., "The generation of human natural killer cells from CD34+/DR− primitive progenitors in long–term bone marrow culture" *Blood* (1992) 80:2182–2187.

Lotzová et al., "Genesis of human oncolytic natural killer cells from primitive CD34+CD33− bone marrow progenitors" *J. Immunol.* (1993) 150:5263–5269.

Lanier et al., "The developmental relationship between NK cells and T cells" *Immunol. Today* (1992) 13:392–395.

Sánchez et al., "Identification of a common T/natural killer cell progenitor in human fetal thymus" *J. Exp. Med.* (1994) 180:569–576.

Taswell, "Limiting dilution assays for the determination of immunocompetent cell frequencies" *J. Immunol.* (1981) 126:1614–1619.

Kaushansky et al., "Promotion of megakaryocyte progenitor expansion and differentiation by the c–Mpl ligand thrombopoietin" *Nature* (1994) 369:568–571.

Bartely et al., "Identification and cloning of a megakaryocyte growth and development factor that is a ligand for the cytokine receptor Mpl" *Cell* (1994) 77:1117–1124.

Fritsch et al., "Rapid discrimination of early CD34+ myeloid progenitors using CD45–RA analysis" *Blood* (1993) 81:2301–2309.

Paul et al., "Stromal cell–associated hematopoiesis: Immortalization and characterization of a primate bone marrow––derived stromal cell line" *Blood* (1991) 77:1723–1733.

Fletcher et al., "Murine leukemia inhibitory factor enhances retroviral–vector infection efficiency of hematopoietic progenitors" *Blood* (1990) 76:1098–1103.

Metcalf et al., "Effects of injected leukemia inhibitory factor on hematopoietic and other tissues in mice" *Blood* (1990) 76:50–56.

Verfaillie et al., "Leukemia inhibitory factor/human interleukin for DA cells: a growth factor that stimulates the in vitro development of multipotential human hematopoietic progenitors" *Blood* (1991) 77:263–270.

Dick et al., "Gene transfer into normal human hematopoietic cells using in vitro and in vivo assays" *Blood* (1991) 78:624–634.

Smith et al., "Inhibition of pluripotential embryonic stem cell differentiation by purified polypeptides" *Nature* (1998) 336:688–690.

Whitlock et al., "Bone marrow stromal cell lines with lymphopoietic activity express high levels of a pre–B neoplasia–associated molecule" *Cell* (1987) 48:1009–1021.

Williams et al., "Myeloid leukaemia inhibitory factor maintains the developmental potential of embryonic stem cells" *Nature* (1988) 336:684–687.

Nichols et al., "Establishsment of germ–line–competent embryonic stem (ES) cells using differentiation inhibiting activity" *Development* (1990) 110:1341–1348.

Metcalf, "The leukemia inhibitory factor (LIF)" *Intl. J. Cell. Clon.* (1991) 9:95–108.

Leary et al., "Leukemia inhibitory factor differentiation–inhibiting activity/human interleukin for DA cells augments proliferation of human hematopoietic stem cells" *Blood* (1990) 75:1960–1964.

Beaucage et al., "Deoxynucleoside phosphoramidites—a new class of key intermediates for deoxypolynucleotide synthesis" *Tetra. Let.* (1981) 22:1859–1862.

Matteucci et al., "Synthesis of deoxyoligonucleotides on a polymer support" *J. Amer. Chem. Soc.* (1981) 103:3185–3191.

Metzger et al., "The human oestrogen receptor functions in yeast" *Nature* (1988) 334:31–36.

Spangrude, "Enrichment of murine haemopoietic stem cells: diverging roads" *Immunol. Today* (1989) 10:344–350.

Andrews et al., "The L4F3 antigen is expressed by unipotent and multipotent colony–forming cells but not by their precursors" *Blood* (1986) 68:1030–1035.

Miller et al., "Improved retroviral vectors for gene transfer and expression" *BioTechniques* (1989) 7:980–990.

van Beusechem et al., "Expression of human adenosine deaminase in mice transplanted with hemopoietic stem cells infected with amphotropic retroviruses" *J. Exp. Med.* (1990) 172:729–736.

Valerio et al., "Retrovirus–mediated gene transfer into embryonal carcinoma and hemopoietic stem cells: expression from a hybrid long terminal repeat" *Gene* (1989) 84:419–427.

Parks et al., "Fluorescence–activated cell sorting: theory, experimental optimization, and applications in lymphoid cell biology" *Meth. Enzymol.* (1984) 108:197–241.

Dalchau et al., "Identification and unusual tissue distribution of the canine and human homologues of THY–1 (P)" *J. Exp. Med.* (1979) 149:576–591.

Bender et al., "Expression of the human β–globin gene after retroviral transfer into murine erythroleukemia cells and human BFU–E cells" *Mol. Cell. Biol.* (1988) 8:1725–1735.

Moreau et al., "Leukaemia inhibitory factor is identical to the myeloid growth factor human interleukin for DA cells" *Nature* (1988) 336:690–692.

Jorgensen et al., "Mapping T–cell receptor–peptide contacts by variant peptide immunization of single–chain transgenics" *Nature* (1992) 355:224–230.

Freshney, *Culture of Animal Cells—A Manual of Basic Technique* (1988) Alan R. Liss, Inc., New York, pp. 60–61, and 139–140.

Fletcher et al., "Leukemia inhibitory factor improves survival of retroviral vector–infected hematopoietic stem cells in vitro, allowing efficient long–term expression of vector–encoded human adenosine deaminase in vivo" *J. Exp. Med.* (1991) 174:837–845.

Bodine et al., "Effects of hematopoietic growth factors on the survival of primitive stem cells in liquid suspension culture" *Blood* (1991) 78:914–920.

Metcalf, "The induction and inhibition of differentiation in normal and leukaemic cells" *Phil. Trans. R. Soc. Lond.* (1990) B327:99–109.

Gross et al., "Endowing T cells with antibody specificity using chimeric T cell receptors" *FASEB J.* (1992) 6:3370–3378.

Nienhuis et al. "Gene transfer into hematopoietic stem cells" *Cancer* (1991) 67(10):2700–2704.

Beutler et al. "Gene transfer in the treatment of hematologic disease" *Experimental Hematology* (1990) 18:857–860.

Johnston et al. "Present status and future prospects for HIV therapies" *Science* (1993) 260:1286–1293.

Mulligan et al. "The basic science of gene therapy" *Science* (1993) 260:926–931.

Culver et al. "Lymphocyte gene therapy" *Human Gene Therapy* (1991) 2:107–109.

Roemer et al. "Concepts and stratgies for human gene therapy" *European J. Biochem.* (1992) 208:211–225.

Fields et al., *Fundamental Virology* (1991) Raven Press, Ltd., New York, pp. 267–290 and 709–723.

Mathé, ed., "Tactics and strategy in cancer treatment" *Recent Results in Cancer Research,* Springer–Verlag, Berlin, pp. 1–227. The title page and table of contents were originally submitted, 1977.

Kato et al., "Isolation and characterization of CD34+ hematopoietic stem cells from human peripheral blood by high–gradient magnetic cell sorting" *Cytometry* (1993) 14:384–392.

Bender et al., "Characterization of chemotherapy mobilized peripheral blood progenitor cells for use in autologous stem cell transplantation" *Bone Marrow Transplantation* (1992) 10:281–285.

Caux et al., "GM–CSF and TNF–α cooperate in the generation of dendritic Langerhans cells" *Nature* (1992) 360:258–261.

Bender et al., "Identification and comparison of CD34–positive cells and their subpopulations form normal peripheral blood and bone marrow using multicolor flow cytometry" *Blood* (1991) 77:2591–2596.

Bernstein et al., "Recombinant human stem cell factor enhances the formation of colonies by CD34+ and CD34+ lin− cells, and the generation of colony–stimulating progeny from CD34+lin− cells cultured with interleukin–3, granulocyte colony–stimulating factor, or granulocyte–macrophage colony stimulating factor" *Blood* (1991) 77:2316–2321.

Karlsson, "Treatment of genetic defects in hematopoietic cell function by gene transfer" *Blood* (1991) 78(10):2481–2492.

Cairo et al., "The in vitro effects of stem cell factor and PIXY321 on myeloid progenitor formation (CFU–GM) from innumomagnetic separated CD34+ cord blood" *Pediatric Res.* (1992) 32(3):277–281.

O'Doherty et al., "Dendritic cells freshly isolated from human blood express CD4 and mature into typical immunostimulatory dendritic cells after culture in monocyte–conditioned medium" *J. Exp. Med.* (1993) 178:1067–1078.

Gore et al., "Normal human bone marrow precursors that express terminal deoxynucleotidyl transferase include T–cell precursors and possible lymphoid stem cells" *Blood* (1991) 77:1681–1690.

Pontvert–Delucq et al., "Characterization and functional analysis of adult human bone marrow cell subsets in relation to B–lymphoid development" *Blood* (1993) 82:417–429.

METHOD OF RECONSTITUTING HUMAN LYMPHOID AND DENDRITIC CELLS

RELATED APPLICATIONS

This application is a continuation of U.S. application Ser. No. 08/464,678 filed on Jun. 6, 1995, now abandoned which is the U.S. national phase of PCT Application Serial No. PCT/US95/03038 filed on Mar. 9, 1995 which is a continuation-in-part U.S. application Ser. No. 08/260,185 filed Jun. 15, 1994, now abandoned.

FIELD OF THE INVENTION

The invention relates to methods of enriching for hematopoietic cell populations enriched in myeloid and/or lymphoid progenitor cells based on cell specific markers. The methods also provide cell populations enriched for progenitors having lymphoid differentiative capacity. Compositions enriched for the cells and populations of cells obtained therefrom are also provided by the invention. Methods of use of the cells are also included.

BACKGROUND OF THE INVENTION

Mammalian hematopoietic (blood) cells provide a diverse range of physiologic activities. Hematopoietic cells are divided into lymphoid, myeloid and erythroid lineages. The lymphoid lineage, comprising B, T and natural killer (NK) cells, provides for the production of antibodies, regulation of the cellular immune system, detection of foreign agents in the blood, detection of cells foreign to the host, and the like. The myeloid lineage, which includes monocytes, granulocytes, megakaryocytes, as well as other cells, monitors for the presence of foreign bodies, provides protection against neoplastic cells, scavenges foreign materials, produces platelets, and the like. The erythroid lineage provides the red blood cells, which act as oxygen carriers.

All publications cited herein are hereby incorporated herein by reference in their entirety.

Despite the diversity of the nature, morphology, characteristics and function of hematopoietic cells, it is presently believed that these cells are derived from a single cell population, termed hematopoietic "stem cells." Unlike more "mature" blood cells, stem cells are capable of self-regeneration but may also divide into progenitor cells that are no longer pluripotent and have a limited self-regeneration. These progenitor cells divide repeatedly to form more mature cells which eventually become terminally differentiated to form the various mature hematopoietic cells. Thus the large number of mature hematopoietic cells is derived from a small reservoir of stem cells by a process of proliferation and differentiation.

Progenitor cells mature into bipotential cells and then become lineage committed, that is, are incapable of maturing into more than one lineage. The use of the words progenitor or progenitor cells indicates cell populations which are no longer stem cells but which have not yet become terminally differentiated. The use of the word lymphoid, myeloid or erythroid in conjunction with progenitor indicates the potential cell populations into which the progenitor is capable of maturing.

Highly purified populations of stem cells currently find use in repopulation of the entire hematopoietic system. Purified progenitor cells of individual lineages would find use in repopulating or augmenting the various lineages. As progenitors are not believed to be extensively self-regenerating, the repopulation or augmentation would be limited.

Stem cells and progenitor cells constitute only a small percentage of the total number of hematopoietic cells. Hematopoietic cells are identifiable by the presence of a variety of cell surface protein "markers." Such markers may be either specific to a particular lineage or be present on more than one cell type. The markers also change with stages of differentiation. Currently, it is not known how many of the markers associated with differentiated cells are also present on stem and progenitor cells. One marker, CD34, is found on stem cells and a significant number of progenitors. U.S. Pat. No. 5,061,620 describes a composition comprising human stem cells.

Table 1 summarizes probable phenotypes of stem cells in fetal, adult, and mobilized peripheral blood. As used herein both infra, supra and in Table 1, the negative sign or, uppercase negative sign, (−) means that the level of the specified marker is undetectable above Ig isotype controls by immunoflow cytometry analysis, and may include cells with very low expression of the specified marker that would be below the sensitivity threshold of the technique.

TABLE 1

| | Natural Killer and T cell markers | | | B cell markers | | | Myelomonocytic Markers | | | Other Markers | | | | | | P-gp |
|---|---|---|---|---|---|---|---|---|---|---|---|---|---|---|---|---|---|
| | CD2 | CD3 | CD8 | CD10 | CD19 | CD20 | CD14 | CD15 | CD16 | CD33 | CD34 | CD38 | HLA-DR | C-Kit | Thy | Rho | Activity |
| Fetal Bone Marrow | − | − | − | − | − | − | − | − | − | ? | + | − | + | + | + | lo | + |
| Adult Bone Marrow | − | − | − | − | − | − | − | − | − | − | + | ? | lo/− | + | + | lo | + |
| Adult Mobilized Peripheral Blood | − | − | − | − | − | − | − | − | − | lo/− | + | ? | lo/− | ? | + | lo | + |

The exact series of differentiation steps which occurs from stem cells to lineage commitment and to terminal differentiation is unknown; likewise, the various subpopulations of cells involved have not been well characterized.

Lymphocytes are highly specialized hematopoietic cells. During the development of the B and T lymphoid lineages, phenotypic and molecular differentiation of primitive cells leads to mature stages where rearrangement of the lymphocyte antigen receptors occur, namely the immunoglobulin (Ig) or T-cell receptor (TCR) chains. Van Noesel and Lier (1993) Blood 82:363–373; and Godfrey and Zlotnik (1993) Immunol. Today 14:547–553. Commitment to the B-cell lineage, expression of the B-cell receptor complex and Ig gene rearrangements take place in the bone marrow or fetal liver. Uckun (1990) Blood 76:1908–1923; and Li et al. (1993) J. Exp. Med. 178:951–960.

In man, the extensive analyses of leukemias, fetal liver and bone marrow have shown that the earliest recognizable population of cells committed to the B lineage express the markers CD34, HLA-DR and CD10 and have intranuclear terminal deoxynucleotidyl transferase activity with Ig genes in germline configuration. Uckun (1990). The marker CD19 is subsequently expressed and remains expressed throughout most later stages of B-cell differentiation, which stages are further identified by the expression of an array of markers including surface Ig. The marker CD2 is transiently found on early B-cell precursors at the time of CD19 expression, so the earliest B-cell precursor can be identified by expression of CD34 and CD10 but in the absence of CD19 and CD2. Uckun (1990). CD10, or CALLA, is a neutral endopeptidase expressed by several hematopoietic and non-hematopoietic cells. LeBien and McCormack (1989) Blood 73:625.

Unlike B-cell differentiation, T-cell development requires passage of T-progenitor cells through the thymus gland to achieve efficient: T-cell receptor (TCR) rearrangement and major histocompatibility complex (MHC)-restriction. At the thymic stage, immature T cells are called thymocytes. The intrathymic stages of T-cell development have been extensively studied in mice and to a lesser extent in man. Godfrey and Zlotnik (1993); Galy et al. (1993) J. Exp. Med. 178:391–401; Terstappen et al. (1992) Blood 79:666–677; and Sanchez et al. (1993) J. Exp. Med. 178:1857–1866. With use of T-cell differentiation assays and multiparameter flow cytometry, it has been shown that CD34 is expressed on the most immature thymocytes which lack cell surface expression of CD1, CD4, CD8 and CD3 antigens. Galy et al. (1993); and Terstappen et al. (1992). CD34 levels decrease while T-cell maturation proceeds, as is the case with maturation along the myeloid, erythroid and B-cell lineages. Terstappen et al. (1991) Blood 77:1218–1227. Studies in animals using mice or quail/chick chimeras and studies in man with constructs of fetal liver and thymus implanted into surrogate severe combined immunodeficiency (SCID) mice, have shown that a constant input of hematopoietic cells is needed to sustain thymopoiesis. Le Douarin and Jotereau (1973) Nature New Biol. 246:25–27; Scollay et al. (1986) Immunol. Rev. 91:129–157; and McCune et al. (1988) Science 241:1632–1639.

The nature of the pro-thymocyte progenitor is however ill-defined. In man, pre-thymic cells with T-cell differentiative capability have been retrieved from various hematopoietic tissues. Intrathymic T-cell reconstitution is achieved following injection of CD34$^+$ cells devoid of lineage-specific antigens (Lin$^-$) isolated from fetal liver (FL). Galy et al. (1993); and Péault et al. (1991) J. Exp. Med. 174:1233–1286. Further fractionation of the CD34$^+$Lin$^-$ FL cells has shown that T-lymphoid potential is present in both the CD7$^-$ and CD7dull subsets. Bárcena et al. (1393) Blood 82:3401–3414. T-cell differentiation can be initiated with CD34$^+$Lin$^-$ fetal bone marrow (FBM) cells and is found in both the CD34$^+$Thy-1$^+$ and CD34$^+$Thy-1$^-$ compartments. Baum et al. (1992) Proc. Natl. Acad. Sci. USA 89:2802–2804.

Differentiation into thymocytes can also be achieved with adult tissues. CD34$^+$Lin$^-$ cells isolated from normal adult bone marrow (ABM) or from the apheresed cytokine-mobilized peripheral blood (MPB) of cancer patients have recently been shown to undergo de novo thymopoiesis and subsequently proceed toward complete maturation into TCRαβ$^+$ and TCRγδ$^+$ T-cells. Galy et al. (1994) Blood 84:104–110.

It has been recently reported that after in utero injection into sheep fetuses, CD34$^+$HLA$^-$DR$^-$ cells isolated from human ABM provide long-term (7 months) multilineage hematopoiesis, including production of mature T-cells and B-cells. Srour et al. (1993) Blood 82:3333–3342. These reports provide a preliminary mapping of pre-thymic T-progenitor cell activity, but the phenotypic composition of the T progenitor cell pool as well as the hierarchical ordering of its components remain largely unexplored.

In contrast, extensive phenotypic fractionation of ABM CD34$^+$ cells has been performed to study myelopoiesis and erythropoiesis. Terstappen et al. (1991); Baum et al. (1992); Lansdorp and Dragowska (1992) J. Exp. Med. 175:1501–1509; Srour et al. (1991) Blood Cells 17:287–295; Craig et al. (1993) J. Exp. Med. 177:1331–1342; and Udomsakdi et al. (1991) Exp. Hematol. 19:338–342. In particular, CD45 isoforms have been useful markers to distinguish primitive from committed myeloid cells. Lansdorp et al. (1990) J. Exp. Med. 172:363–366. CD45 antigens are protein tyrosine phosphatases which exist in various isoforms created by alternative splicing. Thomas (1989) Ann. Rev. Immunol. 7:339–369. The high molecular isoforms (p205–p220) have been designated CD45RA and are not expressed on the cell surface of ABM primitive progenitors having long-term culture initiating-cell (LTCIC) activity. Lansdorp and Dragowska (1992). In contrast, CD45RA is found on less primitive bone marrow progenitors as well as on subsets of mature T-cells where it is thought to correlate with specific functional properties (naive T-cells). Sanders et al. (1988) Immunol. Today 9:195–199.

CD45RA is also expressed on a fraction of thymocytes, particularly on cells at a very early stage of intrathymic development. Deans et al. (1991) J. Immunol. 147:4060–4068. It has actually been speculated with the use of multiparameter flow cytometry that the immediate pre-thymic bone marrow-derived progenitor cells might express CD45RA, but functional evidence has not been provided. Terstappen et al. (1992).

The definitive T cell marker is the T cell antigen receptor (TCR). There are presently two defined types of TCR; TCR-2 is a heterodimer of 2 disulfide-linked transmembrane polypeptides (α and β), TCR-1 is structurally similar but consists of γ and δ polypeptides. The α and β or γ and δ polypeptides form a heterodimer which contains an antigen recognition site. These heterodimers recognize antigen in association with MHC molecules on the surface of antigen-presenting cells. All of these proteins contain a variable region which contributes to the antigen recognition site and a constant region which forms the bulk of the molecule and includes the transmembrane region and cytoplasmic tail. Both receptors are associated with a complex of polypeptides making up the CD3 complex. The CD3 complex comprises the γ, ζ and ε transmembrane polypeptides. The CD3 complex mediates signal transduction when T cells are activated by antigen binding to the TCR.

Approximately 95% of blood T cells express TCR-2 and up to 5% have TCR-1. The TCR-2 bearing cells can be subdivided further into two distinct non-overlapping populations. CD4$^+$ T cells which generally recognize antigens in association with MHC class II molecules, and CD8$^+$ T cells which recognize antigens in association with MHC class I molecules.

A number of markers are carried by B cells but not by resting T cells. The majority of B cells carry MHC class II antigens which are important in cooperation with T cells. Fc receptors for IgG (FcRII, CDw32) are also present.

SUMMARY OF THE INVENTION

The invention relates to methods of enriching for hematopoietic cell populations enriched in myeloid and/or lymphoid and dendritic progenitor cells. The methods also provide cell populations enriched for progenitor cells having myeloid, lymphoid and dendritic cell (DC) or lymphoid and DC differentiative potential. Compositions enriched for the cells and populations of cells obtained therefrom are also provided by the invention. Methods and compositions for genetically modified cells are also provided. Compositions of genetically modified cells are also provided. Methods of use of the cells are also included.

BRIEF DESCRIPTION OF THE DRAWINGS

FIGS. 2E–2H illustrate re-staining of sorted CD34$^+$Lin-CD45RA- cells (FIGS. 2A and 2G) and CD34$^+$Lin$^-$CD45RA$^+$ cells (FIGS. 2F and 2H) for CD33 (FIGS. 2E and 2F) and c-kit (FIGS. 2G and 2H).

FIG. 3A depicts the HLA-donor cells stained with CD19. FIG. 3B depicts HLA-donor cells stained with CD33. FIG. 3C depicts HLA-donor cells stained with CD34. Bones were retrieved 8 weeks after injection of 30,000 CD34$^+$Lin$^-$CD45RA$^-$ cells. Cells were stained with an antibody specific for an HLA determinant of the CD34$^+$Lin$^-$CD45RA$^-$ donor in combination with CD19, CD33 and CD34.

FIGS. 5A and 5B depict the expression on CD10$^+$ cells of CD33/CD19 (FIG. 5A) and CD34/CD10 (FIG. 5B). FIGS. 5C and 5D depict the expression on RA$^+$CD10$^-$ cells of CD33/CD19 (FIG. 5C) and CD34/CD10 (FIG. 5D). FIGS. 5E and 5F depict the expression on RA$^-$CD10$^-$ cells of CD33/CD19 (FIG. 5E) and CD34/CD10 (FIG. 5F).

FIG. 7A shows the expression of the HLA marker specific for host cells in combination with a pan-HLA marker (W6/32). Note the host-derived T-cells expressing high MHC class I antigens. FIGS. 7B and 7C show the expression of the HLA of the host and of CD1a and CD3, respectively. Note that donor-derived thymocytes express high levels of CD1 and graded levels of CD3. FIG. 7D shows the expression of CD4 and CD8 gated on donor cells.

FIG. 9A depicts the progeny of RA$^+$10$^+$ cells stained for CD56 and CD16. FIG. 9B depicts the progeny of RA$^-$10$^-$ cells stained for CD56 and CD16. FIG. 9C depicts the progeny of RA$^+$ cells stained for CD3 and CD56. FIG. 9D depicts the progeny of RA$^-$ cells stained for CD56 and CD33. After 3 weeks, it was possible to identify CD56$^+$CD3$^-$CD16$^-$ NK cells in the cultures of CD45RA$^+$. In contrast, the cultures initiated with CD45RA$^-$ cells contained few CD56$^+$ cells but were mostly composed of CD33$^+$ myeloid cells.

FIG. 10A shows that the majority of cells (>90% in this case) have become CD56$^+$CD3$^-$ NK cells. FIG. 10B shows that the culture conditions did not support the differentiation into CD14$^+$ monocytes or CD19$^+$ B cells.

FIG. 11A shows a representative immunological analysis of NK cells derived from ABM CD34$^+$Lin$^-$CD10$^+$ cell cultures on AC6.21 stroma+ IL-2. Such NK cells express cell surface CD56 but not CD3. FIG. 11B shows the results of two independent $^{51}$Cr release assays using K562 target cells demonstrating the mean dose-dependent cytotoxicity (±SD) of NK cells derived from CD34$^+$Lin$^-$CD10$^+$ ABM cell cultures. Fetal thymocytes cultured in the presence of IL-2 and phytohemagglutinin were used as controls. In FIG. 11B, the closed squares represent ABM CD34$^+$Lin$^-$CD10$^+$ cultures and the open circles represent fetal lymphocyte culture. FIG. 11C shows the results of a limit dilution analysis of ABM CD10$^+$ and CD10$^-$ subsets on AC6.21 cells+IL-2 for 7 weeks. Wells were immunostained and scored for the presence of detectable (≥1% above background) CD56$^+$CD3$^-$ NK cells. In FIG. 11C, the open circles represent CD34$^+$Lin$^-$CD10$^-$ cultures and the closed squares represent CD34$^+$Lin$^-$CD10$^+$ cultures.

FIG. 13A depicts culture initiated with CD34$^+$Lin$^-$CD10$^+$ ABM cells showing the presence of DC with different morphologies.

DETAILED DESCRIPTION OF THE INVENTION

Figure 1:
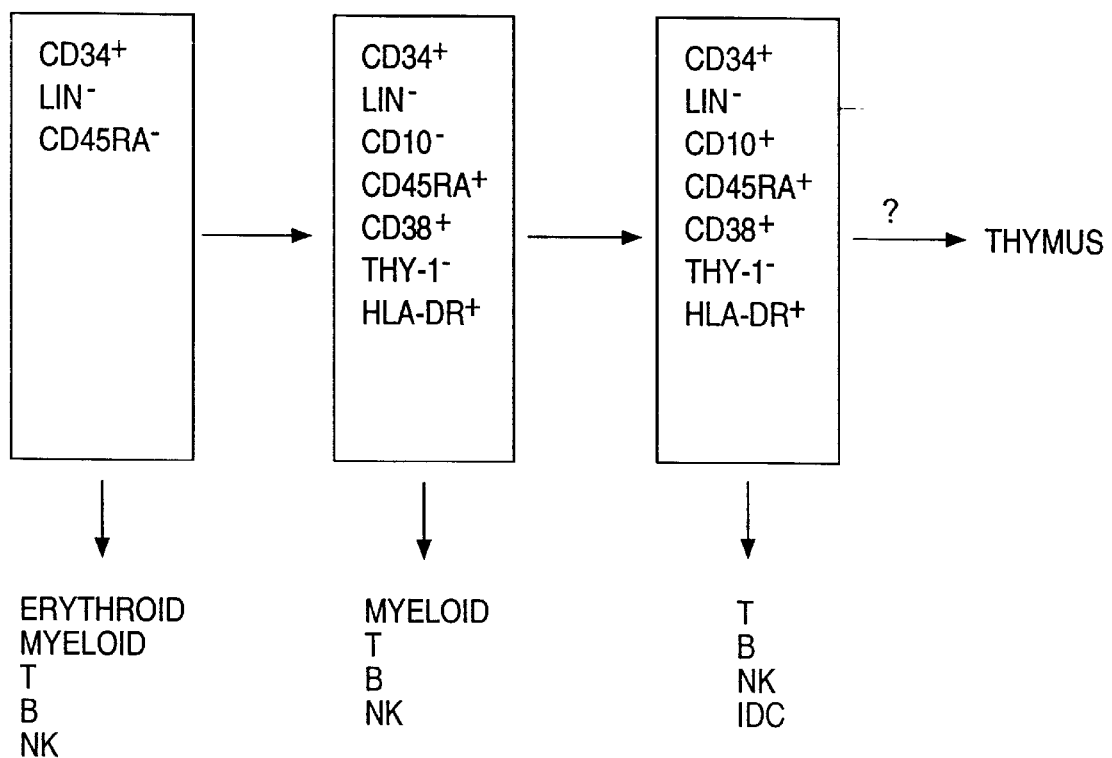
FIG. 1: Schematic diagram of lymphoid maturation as defined by the experiments described herein. Lineage specific markers are CD2, CD4, CD8, CD56, CD16, CD19, CD20 and glycophorin A.
Figure 2A:
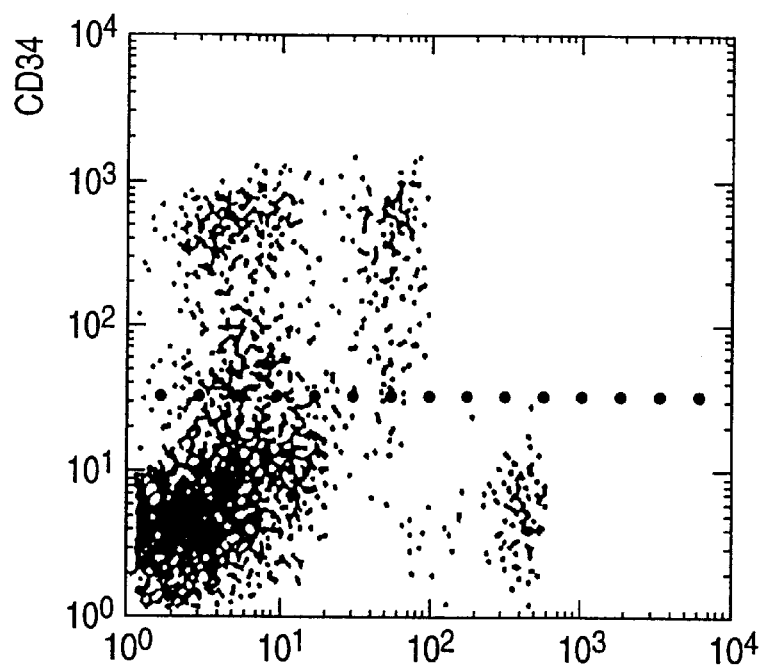
FIG. 2A through FIG. 2H: Phenotypic analysis of CD34$^+$ ABM cells. The expression of CD45RA on ABM cells is represented on the x-axis of each figure. For FIG. 2A on the y-axis CD34 is represented on Lin-gated cells. The y-axis shows the expression of Thy-1, CD38 and HLA-DR on CD34$^+$Lin$^-$ cells for FIGS. 2B, 2C and 2D respectively. Lineage markers were at least CD2, 14, 16, 19, 15 and glycophorin A and most often also included CD4, CD8, CD56 and CD20.
Figure 2B:
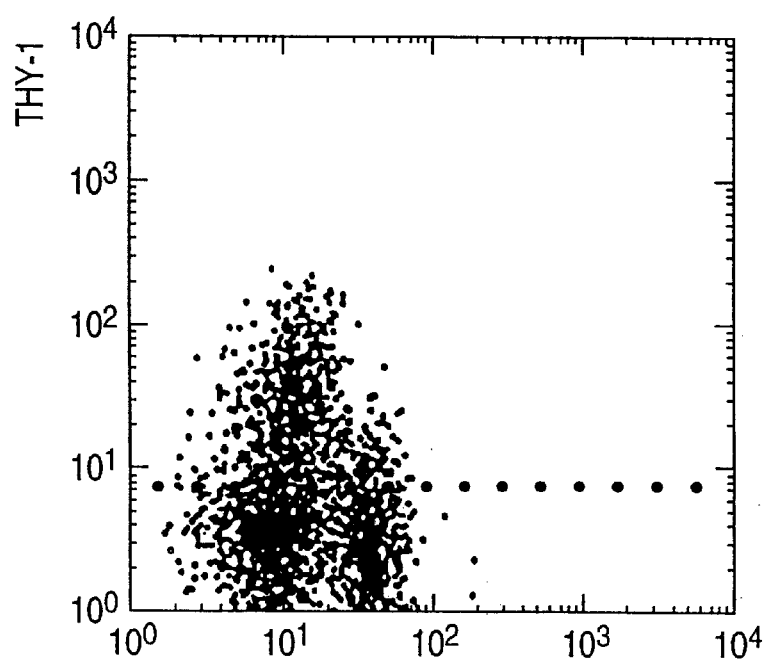
Figure 2C:
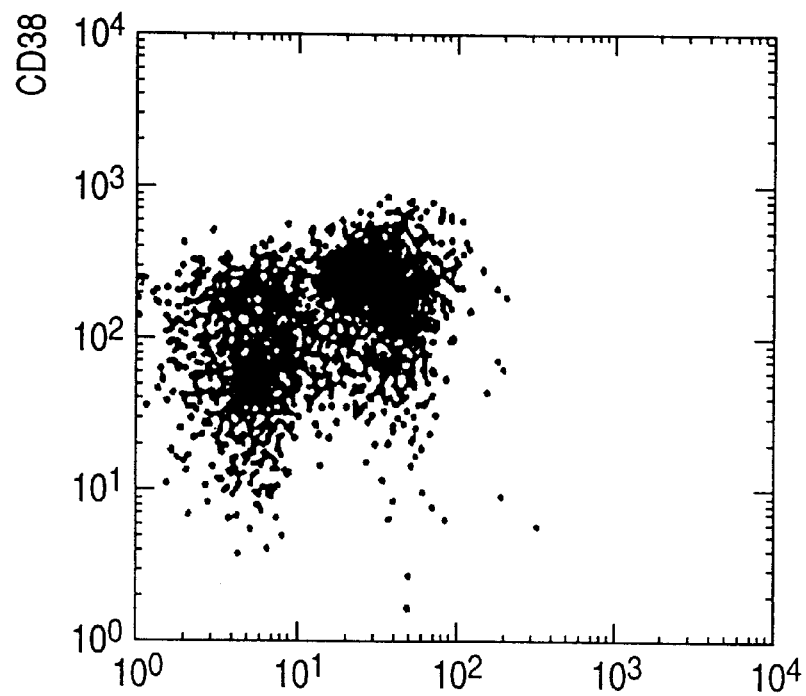
Figure 2D:
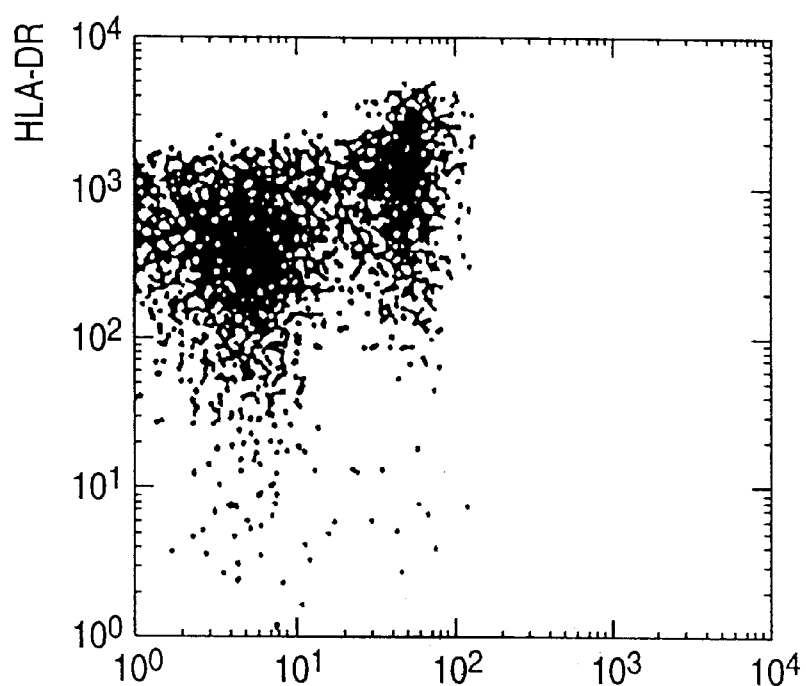
Figure 2E:
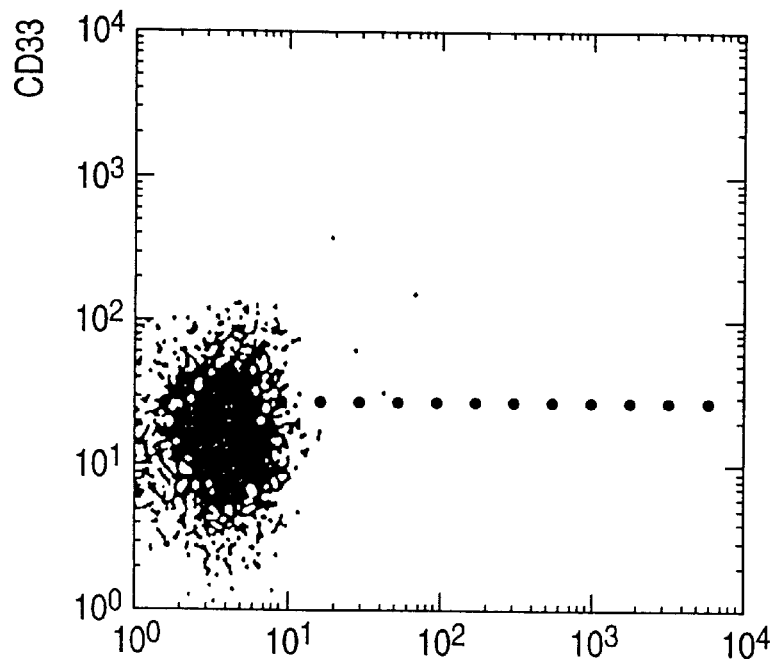
Figure 2F:
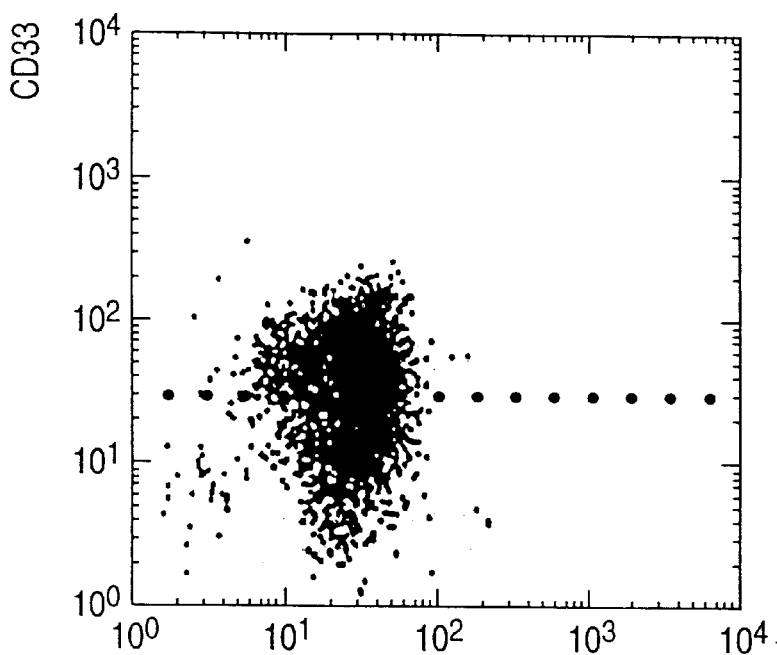
Figure 2G:
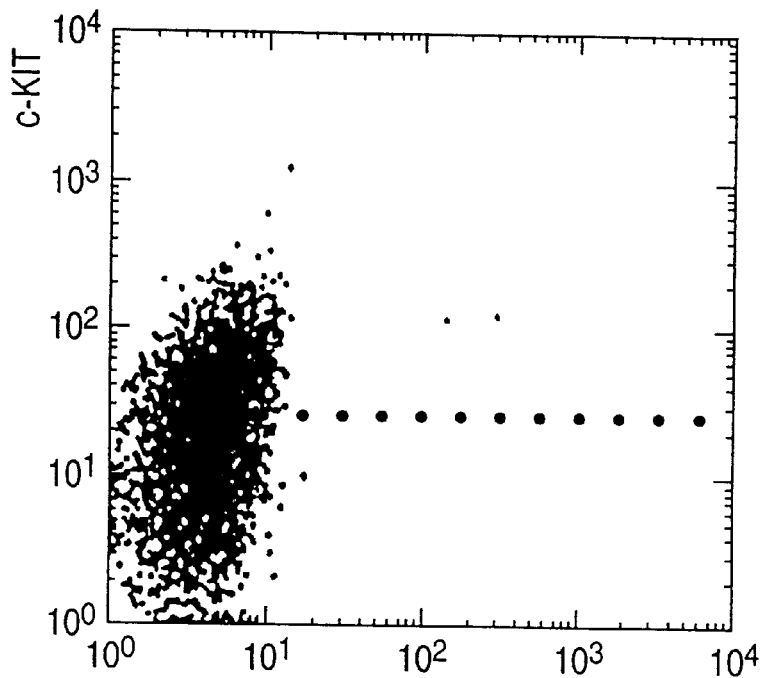
Figure 2H:
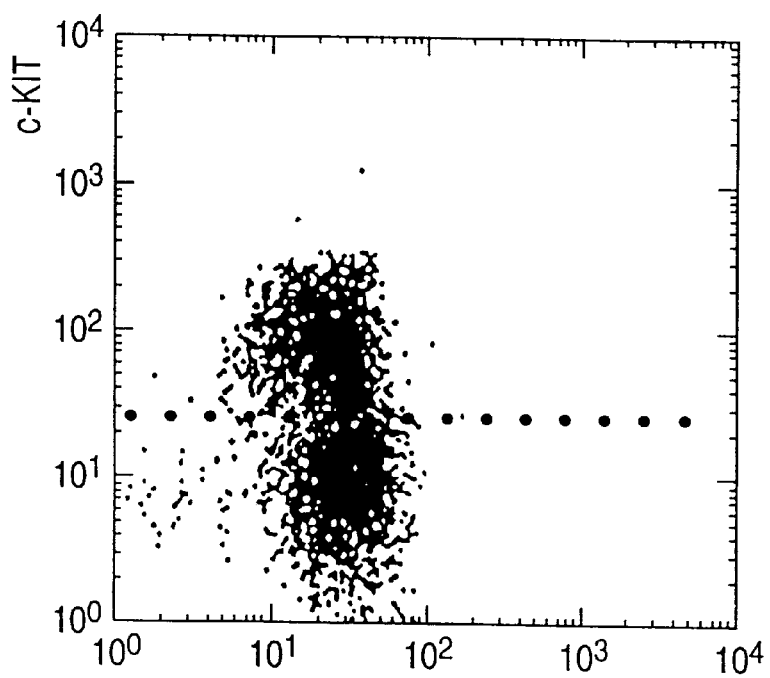

It would be useful to have a system for studying the developmental pathway of the lymphoid lineages. One requirement would be the identification of a lymphoid-restricted progenitor that could give rise to B, T and NK cells. One of the most practical applications is in the understanding and therapy of immunosuppressive diseases such as AIDS or of other diseases of the lymphoid system such as leukemias and lymphomas. Also, as there are no known growth factors or transcription factors implicated in the development, differentiation and growth of lymphoid progenitors, such a system allows for isolation and characterization of such factors. Further, since there is limited understanding of lymphoid gene regulation, particularly at the transcription level, such a system allows for the analysis and characterization of such gene regulation. The identification of these early progenitor populations and of their total myeloid and lymphoid potential will be extremely important to research new cytokines, new cytokine receptors or new transcription factors. The invention described herein provides a mechanism to address these issues.

In order to delineate the steps towards lymphoid commitment from pluripotent stem cells, thymus reconstitution potential was correlated with myeloid, erythroid and B-lymphoid and NK progenitor activities. CD45RA was first used to fractionate CD34$^+$Lin$^-$ adult bone marrow (ABM) cells, and the analysis of lymphoid commitment was refined by examining the T-progenitor cell activity of the earliest B-cell precursor population identifiable. CD10 was then used to further purify the CD45RA$^+$ population, and the resulting cell populations were assessed for their lymphoid progenitor and DC activity.

The results obtained show that there is lymphoid, myeloid, natural killer, and DC progenitor activity in primitive and in committed bone marrow subsets, and that there is a small subset strongly restricted to lymphoid development. Thus, the lymphoid lineages and, importantly, the DC lineage can be segregated from more primitive multipotent stem cells and from erythroid and myeloid progenitor cells.

Although conditions that induce differentiation of human CD34$^+$ cells into DC have been identified (Caux et al. (1994) J. Exp. Med. 180:1263), the developmental pathway and lineage affiliation of DC has been obscure until now. Indeed, DC have long been recognized as a cell type functionally distinct from monocytes/macrophages. This conclusion was based on morphology, phenotype, phagocytic activity, antigen-presenting ability, cytokine production and cellular turnover rates of DC and monocyte/macrophages. Steinman (1991) Ann. Rev. Immunol. 9:271; Macatonia et al. (1993) Int. Immunol. 5:1119; and Kampinga (1990) J. Immunol. 145:1659. There is indirect evidence linking DC to lymphoid cells, based on the isolation in mouse of a common intrathymic progenitor pool and by the expression of several cell surface antigens shared between DC and T cells. Ardavin et al. (1993) Nature 362:761; and Winkel et al. (1994) Immunol. Lett. 40:93. The data provided herein are the first direct evidence that the DC lineage originates from progenitor cells distinct from hematopoietic progenitors which give rise to erythrocytes, monocytes and granulocytes. These results suggest that DC may be developmentally more closely related to lymphoid cells than to myeloid cells.

The invention encompasses compositions enriched for progenitor cells capable of differentiation into myeloid cells, DC and all classes of lymphoid cells, and progenitor cells capable of differentiation into DC and all classes of lymphoid cells. These progenitor cell populations are characterized by the following phenotypes: CD45RA$^+$CD34$^+$Lin$^-$ (hereinafter, RA$^+$) and CD45RA$^+$CD10$^+$Lin$^-$CD34$^+$ (hereinafter, "10$^+$") respectively. The 10$^+$ cells are also termed "central lymphoid progenitors". Other cell populations abbreviated herein are CD45RA$^-$CD10$^-$Lin$^-$CD34$^+$ (hereinafter, "RA$^-$10$^-$"); CD45RA$^+$CD10$^-$Lin$^-$CD34$^+$ (hereinafter, "RA$^+$10$^-$"); and CD45RA$^-$CD34$^+$Lin$^-$ (hereinafter, "RA$^-$"). RA$^+$ cells have myeloid, DC, and lymphoid activity, and can be subdivided by CD10 into RA$^+$10$^+$ and RA$^+$10$^-$. The RA$^+$10$^+$ population is a small subset with differentiative potential restricted to all classes of lymphoid cells and DC.

Thus, the invention encompasses compositions substantially enriched for various progenitor cells. In one embodiment, the enriched cells are RA$^+$, myeloid, DC, and lymphoid progenitors. In another embodiment, the enriched cells are 10$^+$, lymphoid and DC progenitor cells. In another embodiment, the enriched cells are RA$^+$10$^-$, myeloid and lymphoid progenitor cells. The RA$^+$10$^-$ cells may be useful in situations, for instance, where 10$^+$ leukemic cells are present and would otherwise contaminate the RA$^+$ population. Compositions having greater than 80%, usually greater than about 95% RA$^+$ or 10$^+$ cells are described herein. Thus, substantially enriched cells are approximately 80% enriched for those cells expressing the specified markers(s). Preferably, the cells are approximately 80% enriched for the specified marker(s). More preferably, the cells are approximately 80–90% enriched for the specified markers. Most preferably, the cells are 90% enriched for the specified marker(s).

The progenitor cells described herein are capable of differentiating into lymphoid/myeloid/DC lineages and lymphoid/DC lineages. Neither population is capable of differentiating to the erythroid lineage. FIG. 1 provides a schematic of the cell types and their lineage potential. Lin$^-$ cells generally refer to cells which lack markers associated with T cells (such as CD2, CD3, CD4 and CD8), B cells (such as CD19 and 20), myeloid cells (such as CD14, 15 and 16) NK cells (such as CD56 and CD16), and erythrocytes (such as glycophorin A). Preferably, the lineage panel will include at least CD19. Convenient lineage markers to use in addition to CD19 include CD2, CD4 and CD15. Other lineage markers may be used to ensure the removal of more differentiated cells, but their use does not further substantially enrich the progenitor cell population obtained.

Thus, embodiments of the invention are directed to methods of purifying or enriching for these progenitor cells and compositions obtained thereby. The source of cells may be any known in the art, such as the bone marrow, fetal, neonates or adult or other hematopoietic cell source, e.g., fetal liver, peripheral blood or umbilical cord blood.

Selection of these progenitor cells need not be achieved with a marker specific for the cells. By using a combination of negative selection (removal of other committed cells) and positive selection (isolation of cells), enriched cell populations can be achieved.

Various techniques may be employed to separate the cells by initially removing cells of dedicated lineage. Monoclonal antibodies are particularly useful for identifying markers associated with particular cell lineages and/or stages of differentiation.

If desired, a large proportion of terminally differentiated cells may be removed by initially using a "relatively crude" separation. For example, magnetic bead separations may be used initially to remove large numbers of lineage committed cells. Desirably, at least about 80%, usually at least 70% of the total hematopoietic cells will be removed.

Procedures for separation may include but are not limited to, magnetic separation, using antibody-coated magnetic beads, affinity chromatography, cytotoxic agents joined to a monoclonal antibody or used in conjunction with a monoclonal antibody, including but not limited to, complement and cytotoxins, and "panning" with antibody attached to a solid matrix, e.g., plate, elutriation or any other convenient technique.

Techniques providing accurate separation include but are not limited to, flow cytometry, which can have varying degrees of sophistication, e.g., a plurality of color channels, low angle and obtuse light scattering detecting channels, impedance channels, etc.

In a separation, typically starting with about $1 \times 10^{8-9}$, preferably at about $5 \times 10^{8-9}$ cells, the antibody for CD34 may be associated with one fluorochrome, while the antibodies for the various dedicated lineages may be illuminated by different fluorochromes. Fluorochromes which may find use in a multicolor analysis include phycobiliproteins, e.g., phycoerythrin and allophycocyanins; fluorescein and Texas red.

While each of the lineages may be separated in a separate step, desirably the lineages are separated at the same time as one is positively selecting for CD34 and CD45RA and/or CD10. Generally, initial bulk purification steps result in about $1 \times 10^8$ cells. Depletion of lineage specific cells from this population yields about $1–3 \times 10^7$ cells which contain about 10–20,000 $10^+$ cells and $1.5 \times 10^5$ $10^-$ cells. In the $10^-$ cells, about 50,000—$1 \times 10^5$ are $RA^+10^-$ and $1 \times 10^5$ are $RA^-10^-$.

The cells may be selected against dead cells, by employing dyes associated with dead cells (e.g., propidium iodide). Preferably, the cells are collected in a medium comprising 2% fetal calf serum (FCS) or 0.2% bovine serum albumin (BSA).

Other techniques for positive selection may be employed, which permit accurate separation, such as affinity columns, and the like. The method should permit the removal to a residual amount of less than about 20%, preferably less than about 5%, of the non-progenitor cell populations.

While it is believed that the particular order of separation is not critical to this invention, the order indicated is preferred. Preferably, cells are initially separated by a coarse separation, followed by a fine separation, with positive selection of a marker associated with the target cells and negative selection for markers not associated with the target cells. Cells may be selected based on light-scatter properties as well as their expression of various cell surface antigens.

Once the $RA^+$ and/or $10^+$ cells have been isolated, they may be propagated by growing in conditioned medium from stromal cells, such as stromal cells that can be obtained from bone marrow, fetal thymus or fetal liver, and are shown to provide for the secretion of growth factors associated with progenitor cell maintenance, or co-culturing with such stromal cells, where the stromal cells may be autologous, allogeneic or xenogeneic. Before using in the co-culture, the mixed stromal cell preparations may be freed of hematopoietic cells employing irradiation, cytotoxic drugs or appropriate monoclonal antibodies for removal of the undesired cells, e.g., with antibody-toxin conjugates, antibody and complement, etc. Alternatively, cloned stromal cell lines may be used where the stromal lines may be allogeneic or xenogeneic.

The medium employed for the culturing of the cells is conveniently a defined enriched medium, including but not limited to, IMDM (Iscove's Modified Dulbecco's Medium), a 50:50 mixture of IMDM and RPMI, and will generally be composed of salts, amino acids, vitamins, $5 \times 10^{-5}$ M β-mercaptoethanol (β-ME), streptomycin/penicillin and 10% FCS, and may be changed from time to time, generally at least about once to twice per week.

The cells generated from $RA^+$ and $10^+$ cells give rise to T cells in the in vivo assays described below. Myeloid and B cell production is seen in vivo only from $RA^-$ cells; myeloid production is seen in vitro from $RA^-$ and $RA^+$ as a whole; $10^+$ have almost no in vitro myeloid activity. B cell production in short-term in vitro assays is seen in both $RA^+$ and $10^+$. $RA^+$ and $10^+$ cells give rise to NK and DC cells in vitro. In addition, the $RA^+10^-$ cultures gave rise to a small subset of $CD34^+10^+$ cells.

To demonstrate differentiation to T cells, fetal thymus is isolated and cultured for from 4–7 days at about 25° C., so as to deplete substantially the lymphoid population. The progenitor cells to be tested for T cell activity are then microinjected into the thymus tissue, where the HLA of the population which is injected is mismatched with the HLA of the thymus cells. The thymus tissue may then be transplanted into a scid/scid mouse as described in U.S. Pat. No. 5,147,784, particularly transplanting under the kidney capsule.

Specifically, the sorted population can be microinjected into HLA mismatched thymus fragments. After 6–10 weeks, assays of the thymus fragments can be performed and assessed for donor-derived T cells. Thymus fragments injected with cells having T-lymphoid potential generate and sustain $CD3^+$, $CD4^+$, and $CD8^+$ T cells along with their progenitors.

Further demonstration of the differentiative capacity of the various cell populations might be accomplished by the detection of myeloid and NK cell production in the stromal cell assays described in the Examples that follow.

The invention also encompasses methods of use of the $RA^+$ and/or $10^+$ cell populations. Such methods include, but are not limited to, reconstituting or augmenting lymphoid and myeloid or lymphoid cell populations respectively; screening for growth factors responsible for lymphoid and myeloid progenitor cell maturation; identifying markers for progenitor-cell specific antibodies (both polyclonal and monoclonal); identification of lymphoid or myeloid-specific genes; identification of genetic. regulatory sequences specific for the lymphoid lineage; and use in gene therapy.

Reconstitution or augmentation of lymphoid and/or myeloid cell populations is useful in a variety of medical settings. Indications to be treated include, e.g., immunodeficiencies and stem cell transplantations. The progenitor cells are particularly useful during stem cell transplantation to decrease the lag time between the transplantation and repopulation of the hematopoietic cells. Methods of obtaining the progenitor cells are described herein, methods of administering hematopoietic cells to patients are within the skill of one in the art.

Identification of a $10^+$ lymphoid restricted progenitor cell population allows assessment of this population as the origin of disease, e.g. leukemia, and therefore is useful in purging such cells from an autologous graft. The invention also encompasses the use of $RA^+$ or $10^+$ cells as DC progenitors for a variety of purposes. DC are among the most potent antigen-presenting cells in the body and are capable is of inducing a primary immune response. Therefore, DC may be useful as a cellular graft to increase one's ability to mount an immune response. DC or DC precursors may be used in a vaccine strategic whereby the cells are loaded with antigen and injected to induce a specific immune response. Alternatively, the injected cells may be used to induce tolerance to a specific antigen.

The $RA^+$ and $10^+$ cells may be used for a variety of gene therapy approaches where expression of the exogenous genetic capability is desired in lymphoid and/or myeloid lineages. Use of the progenitor cells described herein provide an alternative to stem cell based gene therapy. Progenitor cells will be preferred in cases where it is desired to have temporary rather than permanent expression of the exogenous genetic capability. In addition, use of $10^+$ cells allows expression to be restricted to lymphoid cells. Also, gene transfer is likely to be more efficient in progenitors than in stem cells because progenitor cells cycle more actively than stem cells and retroviral vectors are known to require actively cycling cells for efficient integration of the recombinant DNA.

In addition, it would be advantageous to use lymphoid progenitors compared to using mature lymphoid cells for gene therapy. Currently, T cell gene therapy requires ex vivo expansion of T cells with cytokines. Upon re-infusion, the modified T cells often do not home properly to their target organs and may become trapped in (and cleared by) the lungs, liver or spleen. This improper homing may be due to alteration of the membranes during the ex vivo processing, downregulation of homing receptors, or the like. Ex vivo expansion of T cells is costly, cumbersome and time consuming and thus less than ideal for treatment. Use of modified progenitor cells would obviate the necessity of ex vivo expansion of the effector T cells and thus concerns of altered trafficking and persistence in vivo. In addition, the use of modified progenitors will allow amplification in progeny cell numbers, thereby reducing the need for ex vivo expansion and reducing the frequency of administration.

Genetic diseases associated with hematopoietic cells may be treated by genetic modification of autologous or allogeneic progenitor cells to correct the genetic defect. For example, diseases including, but not limited to, adenosine deaminase deficiency, recombinase deficiency, recombinase regulatory gene deficiency, may be corrected by introduction of a wild-type gene into the cells, either by homologous or random recombination. Other indications of gene therapy are introduction of drug resistance genes to enable normal progenitor cells to have an advantage and be subject to selective pressure, e.g., the multidrug resistance (MDR) gene.

Diseases other than those associated with hematopoietic cells may also be treated, where the disease is related to the lack of a particular secreted product including but not limited to, hormones, enzymes, interferon, factor, or the like. By employing an appropriate regulatory initiation region, inducible production of the deficient protein may be achieved, so that production of the protein will parallel natural production, even though production will be in a different cell type from the cell type that normally produces such protein. It is also possible to insert a ribozyme, antisense or other message to inhibit particular gene products or susceptibility to diseases, particularly hematolymphotropic diseases (e.g., HIV).

Genetic modification of the cells can be accomplished at any point during their maintenance by transducing a substantially homogeneous cell composition with a recombinant DNA construct. Preferably, a retroviral vector is employed for the introduction of the DNA construct into the cell. The resulting cells may then be grown under conditions similar to those for unmodified cells, whereby the modified cells may be expanded and used for a variety of purposes.

For genetic modification of the cells, usually a retroviral vector will be employed, however any other suitable vector or delivery system may be used. These include, e.g., adenovirus, adenoassociated virus and artificial chromosomes derived from yeast. Combinations of retroviruses and an appropriate packaging line are also suitable, where the capsid proteins will be functional for infecting human cells. Various amphotropic virus-producing cell lines are known, including, but not limited to PA12 (Miller et al. (1985) Mol. Cell. Biol. 5:431–437); PA317 (Miller et al. (1986) Mol. Cell. Biol. 6:2895–2902); and CRIP (Danos et al. (1988) Proc. Natl. Acad. Sci USA 85:6460–6464).

Possible methods of transduction include direct co-culture of the cells with producer cells, e.g., by the method of Bregni et al. (1992) Blood 80:1418–1422, or culturing with viral supernatant alone with or without appropriate growth factors and polycations, e.g., by the method of Xu et al. (1994) Exp. Hemat. 22:223–230; and Hughes et al. (1992) J. Clin. Invest. 89:1817.

Also described and provided herein are recombinant T cell receptor (TCR) constructs suitable for use in transducing the cells. Suitable constructs and uses thereof are described in International application no. US94/10033, which is hereby incorporated herein by reference. The recombinant TCR can be put under the control of a T cell specific promoter so that it is only expressed in T cells. For example, the promoter could be Granzyme A or Granzyme B, which would cause the recombinant TCR to be expressed predominantly in NK cells and cytotoxic T lymphocytes (CTLs). Cytotoxic lymphocytes require Granzyme B for the rapid induction of DNA fragmentation and apoptosis in allogeneic target cells. Heusel et al. (1994) Cell 76:977–987. The T-cells derived from transduced cells should home and circulate properly since they have matured in vivo and have not been directly manipulated subsequently ex vivo. They can then be expanded in number by administering cytokines in vivo. Since primarily antigen-activated cells proliferate in response to cytokines, modified T cells recognizing the target antigen should be relatively amplified. Also, it may be possible to get a stronger response from the T cells derived from the transduced cells. If more mature T cells are transduced with the recombinant TCR, they may have a dampened response if they are "memory" cells (i.e. previously exposed to antigens) and, therefore, "biased."

Another advantage to genetically modified progenitor cells over mature T cells would be the ability to express the recombinant TCR in more than one hematopoietic lineage.

For example, since macrophages are known to have the ability to engulf tumor cells, it may be useful to express the recombinant TCR in macrophages.

The constructs can be prepared in a variety of conventional ways. Numerous vectors are now available which provide the desired features, such as long terminal repeats, marker genes, and restriction sites, which may be further modified by techniques known in the art. The constructs will encode a signal peptide sequence in addition to the antigenic specificity region and cytoplasmic signalling sequence, to ensure that the recombinant TCR is properly processed post-translationally and expressed on the cell surface. Preferably, the construct is under the control of a T cell specific promoter. Suitable T cell specific promoters include, but are not limited to, Granzyme A, Granzyme B and CD8.

In one embodiment, the signal transducing region and antigenic specificity region are both obtained from TCRs ("classic TCR"). In another embodiment the constructs encode chimeric polypeptides comprising the signal transducing region obtained from a T cell specific receptor or the Fcγ receptor and an antigen binding portion of an immunoglobulin or of a NK receptor ("chimeric TCR").

The recombinant classic TCRs are functional, preferably full length, TCR α and β or γ and δ polypeptides which have been derived from a T cell with known antigenic specificity. Suitable sources of antigen-specific receptors include, but are not limited to, cytotoxic T lymphocytes, T helper cells and NK cells. In another embodiment, the polypeptides may be recombined so as to form a single functional polypeptide with the Vα and Vβ regions forming the antigen binding site. In another embodiment, the Vα and Vβ regions from different TCRs may be recombined to endow the TCR with a different specificity.

The T cell progeny of the cells containing the recombinant classic TCR polypeptides are "MHC restricted", that is, they will only recognize antigen in the presence of MHC. Thus, when using these cells to treat a patient, the TCRs must be able to recognize the same haplotype as that of the host. It is well within the skill of one in the art to determine if the haplotype of the host will be compatible with a particular TCR. The classic TCR approach is advantageous where the antigen is expressed as a short peptide on the cell surface by processing internally and presented in the groove of an MHC molecule.

In the case of the chimeric TCR, the chimeric molecule contains an antigen binding sequence from an antibody or another receptor, a transmembrane sequence and a sequence that can transduce a signal and elicit a function. A variety of these and related molecules have been cloned and expressed in various T cell lines. Kuwana et al. (1987) Biochem. Biophys. Res. Comm. 149:960–968; Gross et al. (1989) Trans. Proc. 21:127–130; Becker et al. (1989) Cell 58:911–921; Gross et al. (1989) Proc. Natl. Acad. Sci. USA 86:10024–10028; and Goverman et al. (1990) Cell 60:929–939. Several chimeric TCRs have been created and found to be active in targeting T cells to the antigen recognized by the antibody binding site. Eshhar (1993) Proc. Natl. Acad. Sci. USA 90:720–724; and Hwu et al. (1993) J. Exp. Med. 178:361–366.

Suitable signal transducing regions can be obtained from receptors that have activation capacity through a specific chain including, but not limited to, the γ chain of the $F_C$ receptor, the CD3 ζ chain, IL-2 receptor γ chain, CD8 or CD28. Alternatively, the antigen binding domain may be associated with TCR α or β chain constant regions, which will transduce signal via association with endogenous CD3 ζ chain. Preferably, the functional portion of the chimeric molecule is the signalling region of a Fcγ or ζ polypeptide and the antigen binding domain is a variable region of an antibody. The variable region may be either the $V_H$ or $V_L$ regions or, preferably, a single chain recombinant thereof.

Methods for recombination in mammalian cells may be found in Molecular Cloning, A Laboratory Manual (1989) Sambrook, Fritsch and Maniatis, Cold Spring Harbor, N.Y.

The T cell progeny of the cells containing the chimeric TCR molecules, may recognize antigen in the absence of MHC when the antigen binding site is derived from an antibody and thus may not be MHC restricted. These molecules are suitable for use in all hosts regardless of haplotype.

Upon reintroduction of the genetically modified cells into the host and subsequent differentiation, T cells are produced that are specifically directed against the specific antigen. Generally, suitable antigens include those found on virally infected cells, and specific cancer cells. More specifically, suitable antigens include, but are not limited to, viral coat proteins and specific surface proteins of cancer cells.

In many situations, cell immunotherapy involves removal of bone marrow or other source of hematopoietic cells from a human host, isolating the progenitor cells from the source and optionally expanding the isolated cells. Meanwhile, the host may be treated to partially, substantially or completely ablate native hematopoietic capability. The isolated cells may be modified during this period of time, so as to provide for cells having the desired genetic modification. In the case of complete hematopoietic ablation, stem cell augmentation will also be required. After completion of the treatment of the host, the modified cells may then be restored to the host to provide for the new capability. The methods of hematopoietic cell removal, host ablation and stem/progenitor cell repopulation are known in the art. If necessary, the process may be repeated to ensure the substantial repopulation of the modified cells.

The modified cells may be administered in any physiologically acceptable vehicle, normally intravascularly, although they may also be introduced into bone or other convenient site where the cells may find an appropriate site for regeneration and differentiation (e.g., thymus). Usually, at: least $1\times10^5$ cells will be administered, preferably $1\times10^6$ or more. The cells may be introduced by injection, catheter, or the like. If desired, factors may also be included, including, but not limited to, interleukins, e.g. IL-2, IL-3, IL-6, and IL-11, as well as the other interleukins, the colony stimulating factors, such as G-, M- and GM-CSF, interferons, e.g. γ-interferon, erythropoietin.

The following examples are meant to illustrate but not limit the invention. In the examples presented below, the following primary results were obtained. First, it was shown that populations enriched in primitive hematopoietic stem cell activity can generate T cells if introduced at the thymic site. Second, the T cell reconstitution potential seems ubiquitously present in various subsets of $CD34^+$ ABM cells, but can be explained for instance by the lymphoid potential present in the CD45RA compartment. Third, cells other than hematopoietic pluripotent stem cells or other than intrathymic pre-T cells can differentiate into T cells. This is a finding that has not been fully appreciated before. Fourth, a small subset of cells (approximately 5.9±3.7% of $CD34^+Lin^-$ cells) was found that has limited myeloid potential but strong T and B lymphoid progenitor activity ($10^+$). Fifth, the $RA^+10^-$ and $10^+$ cells can differentiate into NK cells. Sixth, the $RA^+10^-$ and $10^+$ cells can differentiate into DC cells.

EXAMPLE 1

Sample Processing and Staining for Flow Cytometry Sorting

Adult bone marrow (ABM) aspirates were obtained from the posterior iliac crest of healthy adult volunteers with consent. Low density (<1.077 g/ml) mononuclear cells (MNC) obtained by gradient centrifugation (Lymphoprep, Nycomed Pharma) were washed twice in staining buffer (SB) consisting of phosphate buffered saline and 0.2% bovine serum albumin (BSA, Sigma) and incubated with 1 mg/ml heat inactivated human gamma-globulin (Gamimune, Miles, Inc.) to block non-specific Fc receptor binding of mouse antibodies. Granulocytes were removed either by incubation with magnetic beads (Dynal M450) coated with anti-CD15 monoclonal antibodies (MAbs), (Medarex), or by freezing in liquid nitrogen in the presence of 10% DMSO (Sigma), 10% fetal calf serum (FCS) (Hyclone) and thawing. Cells were incubated with the following lineage-specific phycoerythrin (PE)-conjugated MAbs: anti-CD2, -CD4, -CD8, -CD56, -CD16, -CD19, -CD20 (Becton Dickinson) and anti-glycophorin A (Amac) (PE-Lin). After 2 washes in SB, cells were incubated with sheep anti-mouse immunoglobulin-coated beads (Dynal), and after exposure to a magnetic field, bead-bound cells were discarded. Anti-CD34 MAbs (Tük-3; Dr. Ziegler, University of Berlin, Berlin, Germany) or IgG3 isotype control MAbs were added at 0.3 μg per $10^6$ cells in a total volume of 0.5 ml SB for 20 min. on ice. Cells were washed twice in SB, then incubated with Texas Red (TR)-conjugated goat anti-mouse IgG3 (GAMγ3: antibodies (Southern Biotechnologies Associates) and FITC-labeled anti-CD45RA MAbs (Becton Dickinson) followed by 2 washes in SB. The cells were sorted on the FACStar Plus cell sorter (Becton Dickinson) equipped with dual argon ion lasers, the primary emitting at 488 nm and a dye laser (Rhodamine 6G) emitting at 600 nm (Coherent Innova 90, Santa Clara, Calif.). All cells expressing PE-Lin levels above the value of the negative control were excluded by electronic gating, and the remainder sorted on the basis of CD34 and of CD45RA.

For the CD38 sorts, cells were stained with anti-CD34 (Tük-3) MAbs recognized by TR conjugate GAMγ3, FITC-Lin MAbs (Lin=CD2, CD14, CD15, CD16, CD19 and glycophorin A) and PE anti-CD38 MAbs (Becton Dickinson). For the Thy-1 sorts, cells were labelled with anti-CD34 and anti-Thy-1 MAbs (GM201) recognized respectively by isotype specific TR-GAMγ3 antibodies (Southern Biotechnologies Associates) and PE-anti-mouse IgG1 antibodies (Caltag, South San Francisco, Calif.) then, after extensive blocking with mouse IgG1 (Sigma), FITC-Lin MAbs (Lin=CD2, CD14, CD15, CD16, CD19 and glycophorin A) were added. For HLA-DR sorts, only FITC-CD15 was used as Lin marker with PE-anti-HLA-DR MAbs (Becton Dickinson). For the CD34/CD45RA/Thy-1 isolations, 2 consecutive sorts were performed. First cells were labelled with anti-CD34, anti-Thy-1 and FITC-Lin MAbs as described above. CD34$^+$Lin$^-$ cells sorted with good purity (>90%) were stained again with FITC-CD45RA MAbs and a second sort was performed on the basis of CD45RA and Thy-1 expression.

For the CD10 study, most ABM samples tested were first submitted to a CD34 positive selection using a biotinylated anti-CD34 and a biotin competition system as described in patent application WO 9402016. Positively selected CD34$^+$ cells were stained with anti-CD34 Tük-3 MAbs (recognizing an epitope different from the one used to positively select the cells) and TR goat antimouse (GAM)-γ3, PE-Lin (CD2, CD4, CD8, CD56, CD16, CD19, CD20 and glycophorin A) plus CD10-FITC or relevant control MAbs as described above. To obtain CD45RA subsets devoid of CD10$^+$ cells, two consecutive sorts were performed. First, CD34$^+$CD10$^+$Lin$^-$ and CD34$^+$CD10$^-$Lin$^-$ cells were sorted. The later population was re-stained with either FITC isotype controls or with anti-CD-45RA FITC MAbs, and CD34$^+$Lin$^-$CD10$^-$CD45RA$^-$ and CD34$^+$Lin$^-$CD10$^-$CD45RA$^+$ subsets were sorted. In some experiments, CD34 Mabs (Tük3) were directly conjugated with sulforhodamine.

EXAMPLE 2

Phenotypic Analyses of CD34$^+$ Cell Subsets Cell Populations

Sorted CD34$^+$Lin$^-$ cells were re-stained with PE-conjugated anti-CD38 and anti-HLA-DR MAbE; (Becton Dickinson). Sorted CD34$^+$Lin$^-$CD45RA$^+$ or CD34$^+$Lin$^-$CD45RA$^-$ cells were re-stained with PE-conjugated anti-CD33 MAbs (Becton Dickinson) or with anti-c-kit MAbs (Amac) recognized by a PE-conjugated goat anti-mouse IgM antibody (Southern Biotechnologies Associates). Appropriate isotype controls were also used to ascertain the specificity of the stainings and establish the background from the sort (below 1% in the PE channel on the samples examined).

1. Phenotypic analyses.

CD45RA antigens are prominently expressed on a variety of bone marrow cells. Lansdorp and Dragowska (1992); and Schwinzer (1989) in: Leukocyte Typing IV. White Cell Differentiation Antigens (Knapp et al. eds.) Oxford University Press, New York, pp. 628–634. The CD34$^+$Lin$^-$ ABM cells in the lymphoblastoid gate are clearly divided into two populations based on CD45RA expression (FIG. 2-panel A). As shown, the CD34$^+$Lin$^-$CD45RA$^+$ cells express an intermediate level of the CD45RA antigen, lower than found on some CD34$^-$ cells. CD34$^+$Lin$^-$CD45RA$^+$ cells expressed negative to dull levels of Thy-1 (FIG. 2-panel B), high levels of CD38 and of HLA-DR (FIG. 2-panels C and D), and contained cells with either clearly positive or negative levels of CD33 and of c-kit antigens (FIG. 2-panels E–H). The CD34$^+$Lin$^-$CD45RA$^-$ cells expressed more homogeneously low levels of c-kit and CD33, but were heterogeneous for expression of Thy-1, CD38 and HLA-DR. Cells with negative to dull levels of CD38 and of HLA-DR were mostly found in the CD45RA$^-$ population. Primitive hematopoietic stem cells have been characterized by independent laboratories to be Thy-1$^+$, CD38low, c-kitlow, CD33low and HLA-DRlow, and integration of these parameters shows that they are found in the CD45RA$^-$ compartment of CD34$^+$ ABM cells as previously reported. Terstappen et al. (1991); Baum et: al. (1992); Lansdorp and Dragowska (1992); Srour et al. (1991); Craig et al. (1993); Gunji et al. (1993) Blood 82:3283–3289; and Mayani and Lansdorp (1994) Blood 83:2410–2417.

No detectable cell met all of the phenotypic criteria for primitive hematopoietic stem cells in the CD34$^+$Lin$^-$CD45RA$^+$ compartment which therefore seems to contain progenitors only. The CD45RA$^+$ CD10$^+$ central lymphoid progenitor was further characterized by examination of staining with a number of antibodies and showed that these cells are CD38$^+$HLA-DR$^+$ and Thy-1$^-$ as indicated from the results presented in FIG. 2.

Markers of immature T cells such as CD7, CD5 and CD25 were not significantly expressed on CD34$^+$Lin$^-$CD10$^+$ ABM cells and the c-kit receptor was not detectable on CD34$^+$ Lin$^-$CD10$^+$ (Table 2). A variety of hematopoietic assays were used to determine the differentiative capacity of this CD34$^+$Lin$^-$CD10$^+$ cell population which constitutes 5.9±3.7% (n=13) of CD34$^+$Lin$^-$ ABM cells and approximately 0.09% of ABM mononuclear cells isolated by Ficoll gradient centrifugation.

TABLE 2

Phenotypic characterization of CD34$^+$Lin$^-$CD10$^+$ ABM cells

| Cell surface antigen | Expression on CD34$^+$Lin$^-$CD10$^+$ cells % ± SD (n) |
| --- | --- |
| CD45RA | 100 ± 0 (2) |
| CD38 | 97 ± 3 (2) |
| HLA-DR | 99 ± 1 (2) |
| Thy-1 | 11 ± 9 (3) |
| c-Kit | 1 ± 1 (2) |
| CD7 | 12 ± 4 (2) |
| CD5 | 1 ± 2 (3) |
| CD25 | 0 ± 0 (3) |

To obtain the results depicted in Table 2, phenotypic analysis was performed on CD34$^+$Lin$^-$ cells isolated by flow cytometry to >98% sort purity. Sorted cells were stained with fluorescein or PE-conjugated mAbs anti-CD45RA, CD38, HLA-DR, CD7, CD5, CD25 (Becton Dickinson) and mAbs anti-CD10 conjugated to fluorescein (Becton Dickinson) or PE (Amac). Mabs to Thy-1 (clone GM201) and c-kit (Amac) were used in an indirect method with isotype specific PE-labeled secondary reagents and appropriate blocking. Lin=CD2, CD4, CD8, CD16, CD56, CD19, CD20, CD14 and glycophorin A. In Table 2, results are expressed as % cells positive after subtraction of background staining with IgG1+IgG2a control (for direct staining) and IgG1+IgM (for indirect staining) ±standard deviation (SD) and the number of experiments as indicated in parentheses.

EXAMPLE 3

Myelo-erythroid Progenitor Cell Content, Proliferative Potential and in vivo Marrow Repopulating Ability of CD34$^+$ Cell Subsets 1. Methylcellulose Colony Formation Assay Cells were mixed at a concentration of 500 CD34$^+$ cells per ml of Iscove's methylcellulose (Terry Fox Laboratory) supplemented with purified recombinant human cytokines, c-kit ligand (KL) (10 ng/ml) (R & D Systems), GM-CSF and G-CSF (each at 25 ng/ml) (Amgen), IL-3 (10 ng/ml) (Sandoz Pharma) and erythropoietin (1.2 U/ml) (R & D Systems). When cultured cells were tested, the cell number plated was adjusted to be equivalent to 500 CD34$^+$ cells per ml, as calculated by immunostaining with PE-anti-CD34 (HPCA-2, Becton Dickinson). For each cell type tested, duplicate or more often quadruplicate plates were incubated at 37° C., 5% CO$_2$ in humidified atmosphere for 2 weeks. Burst forming units-erythroid (BFU-E), colony forming units (CFU) composed of monocytes only (CFU-M), or of monocytes and granulocytes (CFU-GM) or comprising all classes of granulocytic and monocytic progenitors (CFU-C) and colonies comprising granulocytes, monocytes and erythroid cells (CFU-mix) were scored using an inverted microscope (Nikon, Tokyo, Japan).

2. In vitro co-culture on AC6.21 cells for myeloid and B-cell differentiation.

AC6.21 stromal cell monolayers were established one week prior to the experiment by plating 1×10$^4$ AC6.21 cells per well of a 96-well flat bottom plate in 100 μl of medium consisting of 50% IMDM (JRH Biosciences), 50% RPMI with 10% FCS (Hyclone), 4×10$^{-5}$ M (2-mercaptoethanol, 10 mM HEPES, penicillin (100 U/ml), streptomycin (100 μg,/ml) (P/S) and 4 mM glutamine (JRH Biosciences). Sorted cells were distributed at 100 cells per well on the pre-established AC6.21 cell monolayer in medium containing IL-3 (10 ng/ml), IL-6 (10 ng/ml) and leukemia inhibitory factor (LIF) (50 ng/ml) (Sandoz Pharma). Half of the cytokine-containing medium was replaced weekly. At the end of the three week long culture, cells were harvested by pipetting, counted and transferred to subsequent assays.

3. SCID-hu bone assay.

C.B-17 scid/scid (SCID) mice bred in our facilities were used between 6 to 8 weeks of age for the construction of SCID-hu bone mice according to the method described by Kyoizumi et al. (1992) Blood 79:1704–1711. Briefly, split fetal long bones were implanted subcutaneously into the mammary fat pads of SCID mice under anesthesia. HLA immunophenotyping of the recipient fetal bone and of donor ABM cells was performed with FITC-conjugated MA2.1, BB7.2, GAP-A3 and W6/32 MAbs derived from hybridomas obtained from the American Type Culture Collection (ATCC). SCID-hu bone mice were used 8 weeks post-implantation as recipients for HLA-mismatched sorted cell populations and were conditioned by receiving a single whole body irradiation dose (400 cGy from a $^{137}$Cs source, Gamma Cell 40, J.L. Shepherd & Associates). Sorted cells (3×10$^4$ in 10 μl) were then injected directly into the transplanted bone using a Hamilton syringe. After 8 weeks, mice were sacrificed and human bones were removed. Flushed bone cells were resuspended into a red blood cell lysing solution, then washed twice in SB and counted before being stained for two-color immunofluorescence with FITC-labeled MAbs against the specific donor HLA allotype in combination with PE anti-CD19, -CD33, and -CD34. FITC and PE-conjugated irrelevant mouse immunoglobulins were used as negative controls. Cells were analyzed on a FACS-can fluorescent cell analyzer (Becton Dickinson).

4. Myeloid and erythroid potential of CD45RA subsets.

Earlier reports have described that erythroid progenitors and LTCIC activities are enriched in CD34$^+$CD45RAlow ABM cells. Lansdorp and Dragowska (1992). Because we are using a panel of lineage markers, it was necessary to assess the myeloid progenitor activities of our populations of study. The results obtained are shown in Table 3 where results are expressed as mean number of colonies per 1,000 total cells plated.

TABLE 3

Methylcellulose Colony Formation Assays

|  |  | CFU-C | BFU-E | CFU-mix |
| --- | --- | --- | --- | --- |
| Pre-culture |  |  |  |  |
| Tissue 1 | RA$^+$ | 102 | 2 | 0 |
|  | RA$^-$ | 70 | 82 | 3 |
| Tissue 2 | RA$^+$ | 48 | 0 | 0.5 |
|  | RA$^-$ | 49 | 58 | 7 |
| Tissue 3 | RA$^+$ | 80 | 0 | 0 |
|  | RA$^-$ | 129 | 78 | 6 |
| Post-AC6.21 culture |  |  |  |  |
| Tissue 4 | RA$^+$ | 3 | 0 | 0 |
|  | RA$^-$ | 12 | 0.2 | 0 |
| Tissue 5 | RA$^+$ | 1.5 | 0 | 0 |
|  | RA$^-$ | 17 | 0 | 0 |

TABLE 3-continued

Methylcellulose Colony Formation Assays

|  |  | CFU-C | BFU-E | CFU-mix |
|---|---|---|---|---|
| Tissue 6 | RA$^+$Thy-1$^-$ | 0.3 | 0 | 0 |
|  | RA$^-$Thy-1$^+$ | 9 | 1.5 | 0.3 |
| Tissue 7 | RA$^+$Thy-1$^-$ | 0.2 | 0 | 0 |
|  | RA$^-$Thy-1$^+$ | 11 | 14 | 0.5 |

The clonogenic potential in the methylcellulose assay showed that CFU-mix and BFU-E were significantly enriched in the RA$^-$ cells, confirming earlier findings. Lansdorp and Dragowska (1992).

Co-cultivation of ABM subsets on the murine bone marrow stromal cell line AC6.21 was done in the presence of IL-3, IL-6 and LIF. The addition of cytokines to the co-culture was necessary to observe optimum growth of adult cells. After 3 weeks, both RA$^-$ and RA$^+$ cells expanded well (respectively 100- to 500- and 70- to 200-fold the input cell number in 3 experiments), and both subsets produced visibly differentiated cells; however, cultures of RA$^-$ cells displayed more clusters of small blasts resembling cobblestone areas.

To circumvent bias from the addition of cytokines and from the relatively early time point chosen for analysis, cultures were immunophenotyped for the presence of CD34$^+$Lin$^-$ cells and their secondary CFU activity measured. RA$^-$ cultures clearly and consistently contained more CD34$^+$Lin$^-$ cells with better maintenance of secondary clonogenic potential than the RA$^+$ cultures. The results obtained are shown in Table 4 and Table 3, post-AC6.21 culture. In Table 4, the cells used in Experiments 4 and 5 were also CD10$^-$. In addition, the RA$^-$ cultures consistently maintained a proportion of CD34$^+$CD45RA$^-$ cells while differentiating into CD34$^+$CD45RA$^+$ cells. In the RA$^+$ cultures all CD34$^+$ progeny cells expressed CD45RA.

TABLE 4

|  | % CD34$^+$Lin$^-$ | | % CD19$^+$ | | % CD33$^+$ | |
|---|---|---|---|---|---|---|
| Experiment | RA$^+$ | RA$^-$ | RA$^+$ | RA$^-$ | RA$^+$ | RA$^-$ |
| 1 | 3.5 | 13.6 | 1.2 | 0.1 | 93 | 95 |
| 2 | 0.5 | 4.0 | N.D. | N.D. | N.D. | N.D. |
| 3 | 0.5 | 1.7 | 0.4 | 0 | 94 | 97 |
| 4 | 0.6 | 2.0 | 0.4 | 0.1 | 91 | 97 |
| 5 | 3.0 | 12.5 | 3.0 | 0 | 83 | 90 |

Hierarchy in the primitiveness of these subsets can be inferred from that analysis to deduce that RA$^-$ cells are most immature and can directly differentiate into RA$^+$ progeny.

Figure 3A:
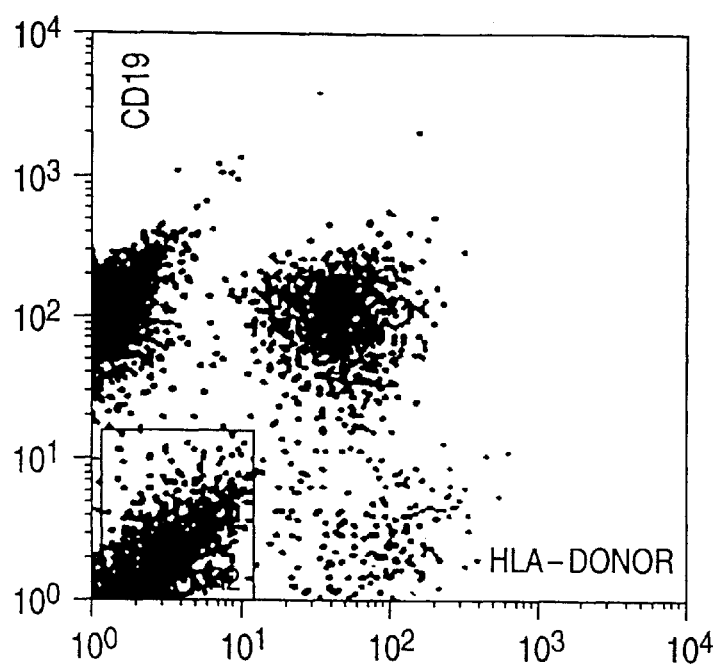
FIG. 3A through FIG. 3C: Phenotypic composition of SCID-hu bones reconstituted with CD34$^+$Lin$^-$CD45RA$^-$ cells.
Figure 3B:
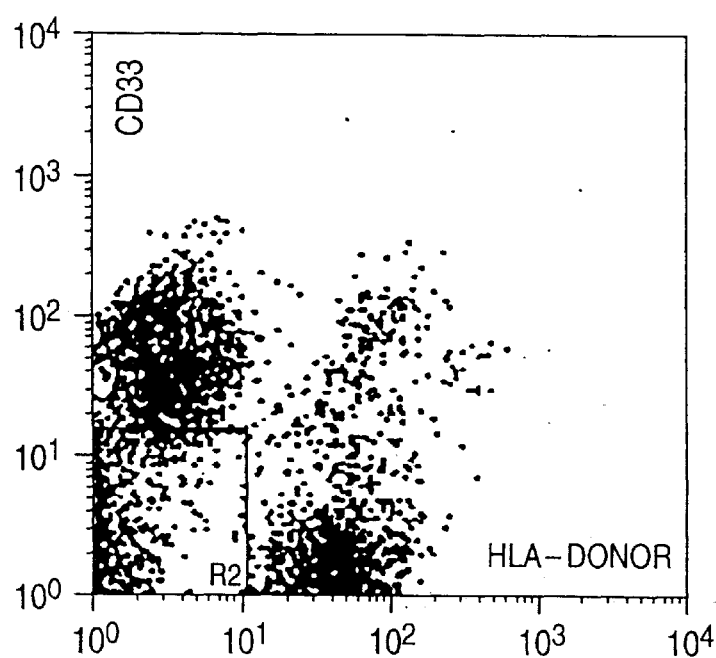
Figure 3C:
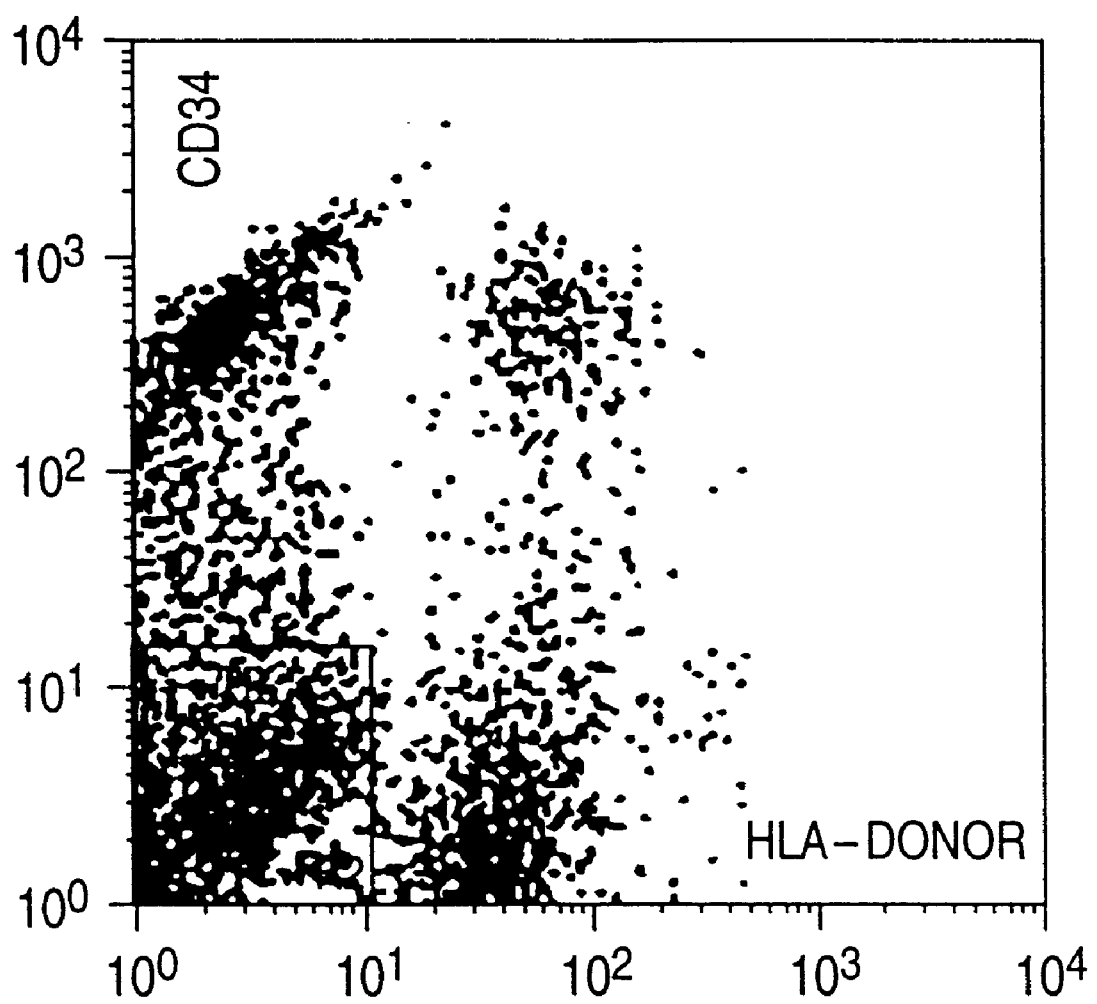

Finally, the long-term hematopoietic reconstitution potential of the CD45RA subsists was examined in the in vivo SCID-hu bone assay which supports long-term multilineage hematopoiesis. DiGiusto et al. (1994). Sorted cells were injected into fragments of human bones preimplanted into surrogate SCID mice. After 8 weeks, the RA$^-$ cells had engrafted as evidenced by the presence of donor-derived CD19$^+$ B-cells, CD33$^+$ myeloid cells and CD34$^+$ progenitor cells (FIG. 3). No progeny were recovered from the RA$^+$ subset although the cell dose tested is known to allow consistent engraftment of CD34$^+$Lin$^-$ cells. Therefore, although RA$^+$ cells contain myeloid and B-lymphoid progenitor activity as determined from in vitro co-culture and methylcellulose assays, this population is lacking the more primitive stem cells required for engraftment in the SCID-hu bone assay.

Taken together, these data confirm and extend earlier observations, showing that the most primitive-hematopoietic activity among the myeloid, erythroid and B-lymphoid lineages is found in the RA$^-$ population. At the same time it is clear that the RA$^+$ cells are devoid of stem cells and erythroid progenitors but contain myeloid progenitors.

5. Fractionation of the RA$^+$ subset.

Figure 4:
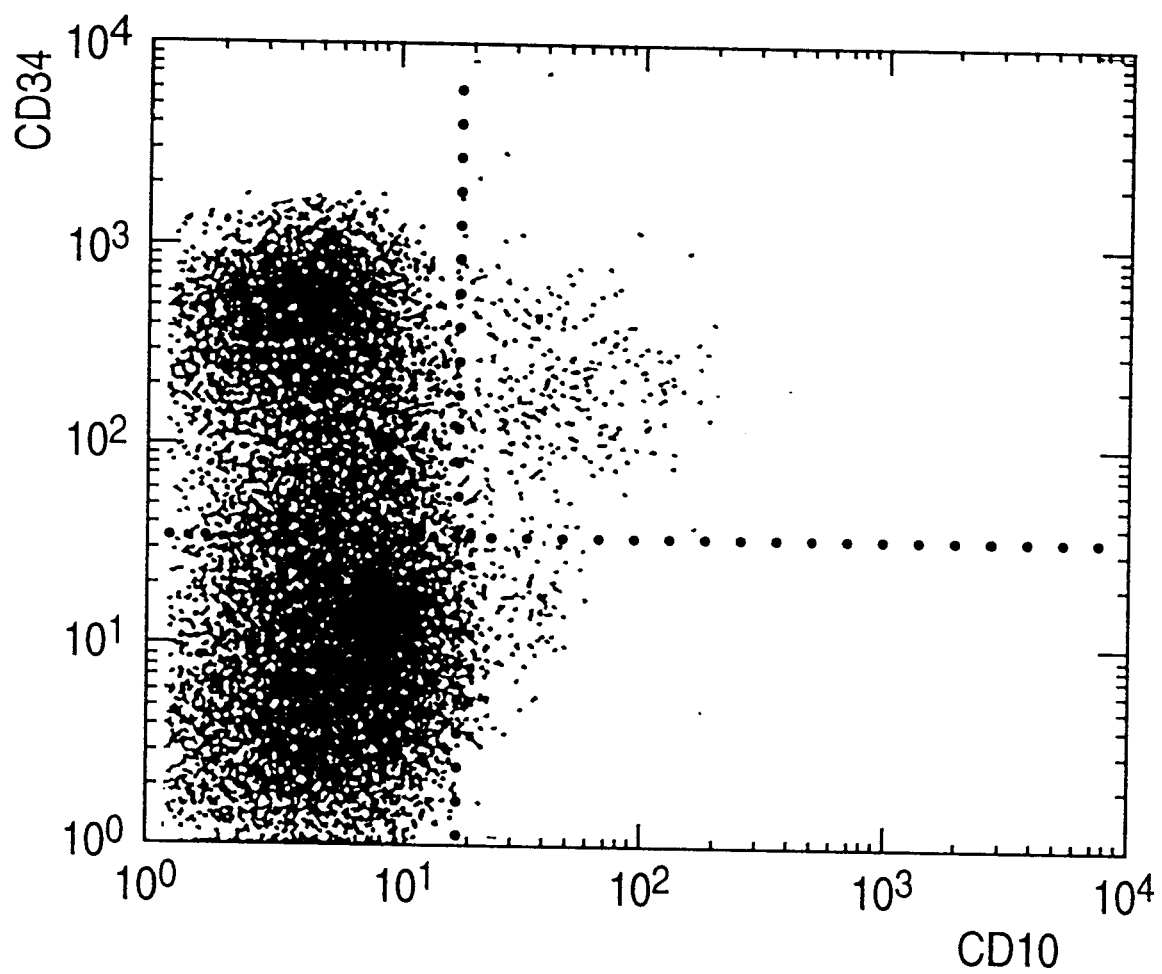
FIG. 4: Expression of CD34 and CD10 on Lin$^-$ (Lin= CD2, CD4, CD8, CD56, CD16, CD19, CD20 and glycophorin A) ABM cells. Cells in the upper right-hand quadrant delineated by the broken lines, were 2% of CD34$^+$Lin$^-$ cells. The average % of CD10$^+$ cells in CD34$^+$Lin$^-$ ABM cells was 5.9±3.7% (n=13 ABM examined).
Figure 5A:
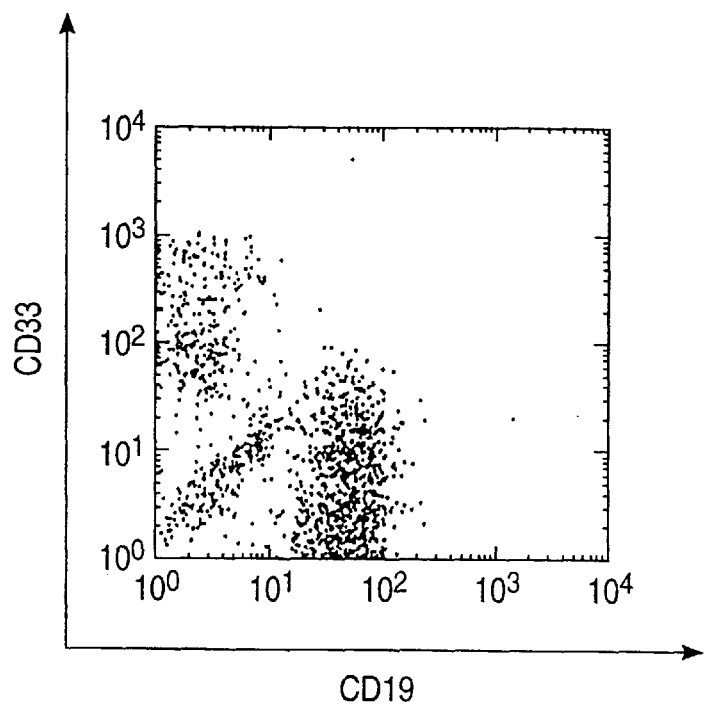
FIG. 5A through FIG. 5F: Phenotypic analysis of AC6.21 culture. Cultures were seeded with 100 cells per well from the CD34$^+$Lin$^-$CD10$^+$ or CD34$^+$Lin$^-$CD45RA$^-$ populations in the presence of IL-3, IL-6 and LIF, and harvested after 3 weeks. Cells were immunostained with CD33 and CD19, or CD34 and CD10.
Figure 5B:
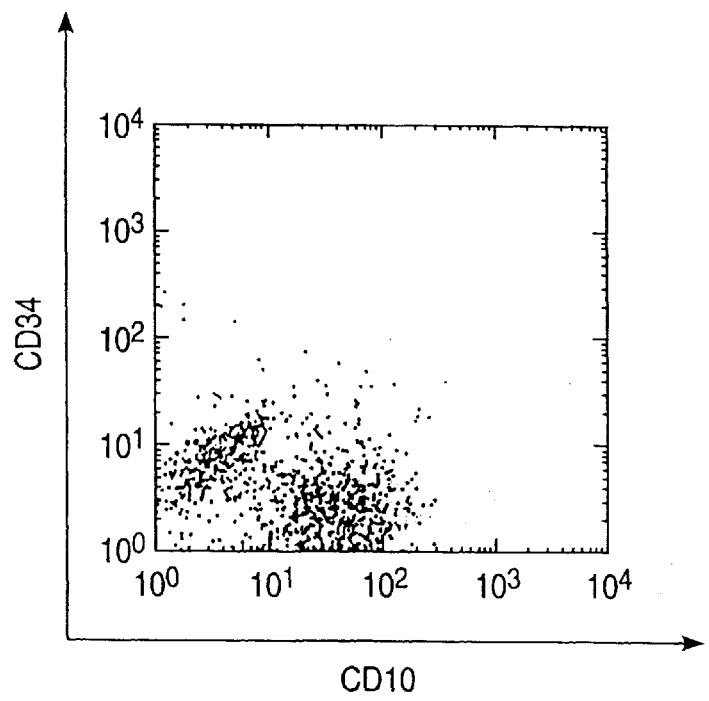
Figure 5C:
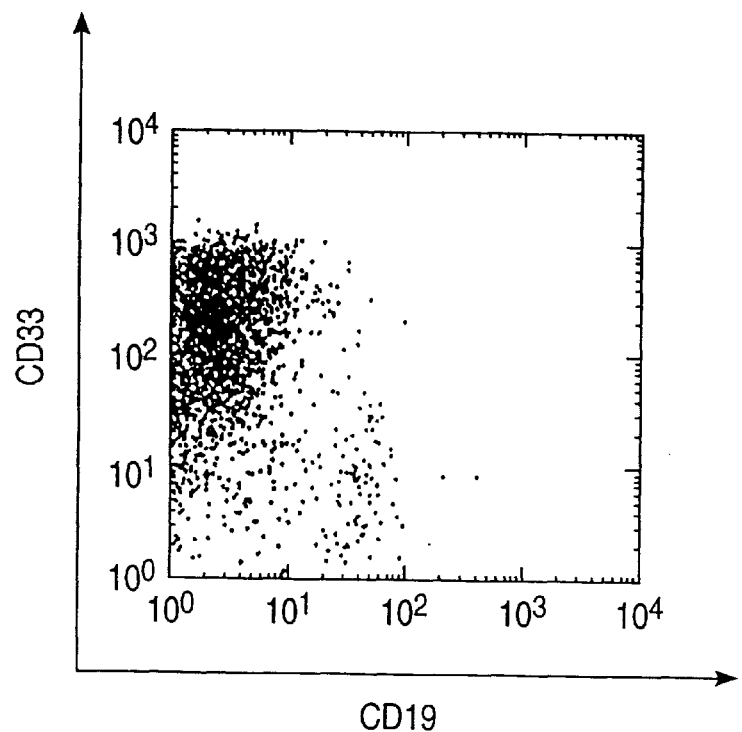
Figure 5D:
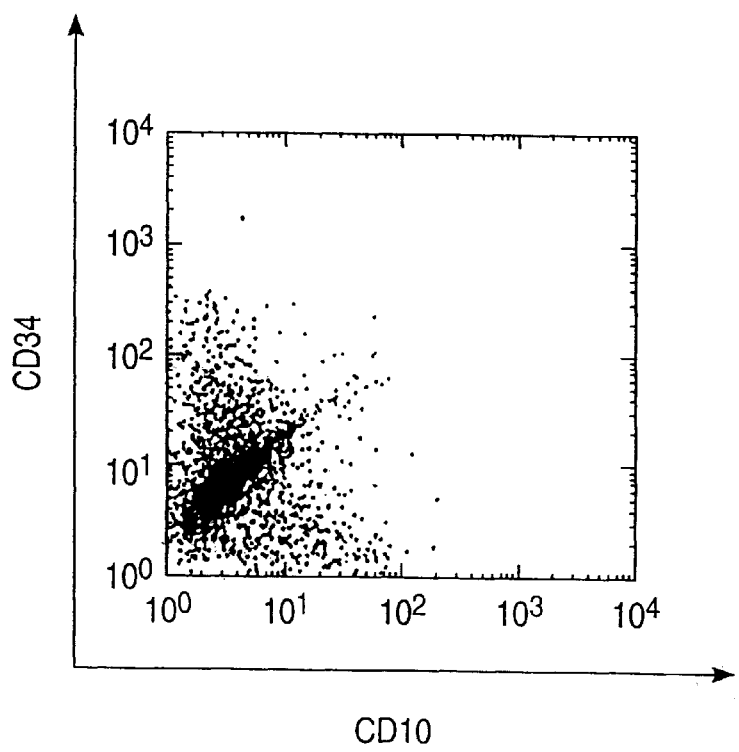
Figure 5E:
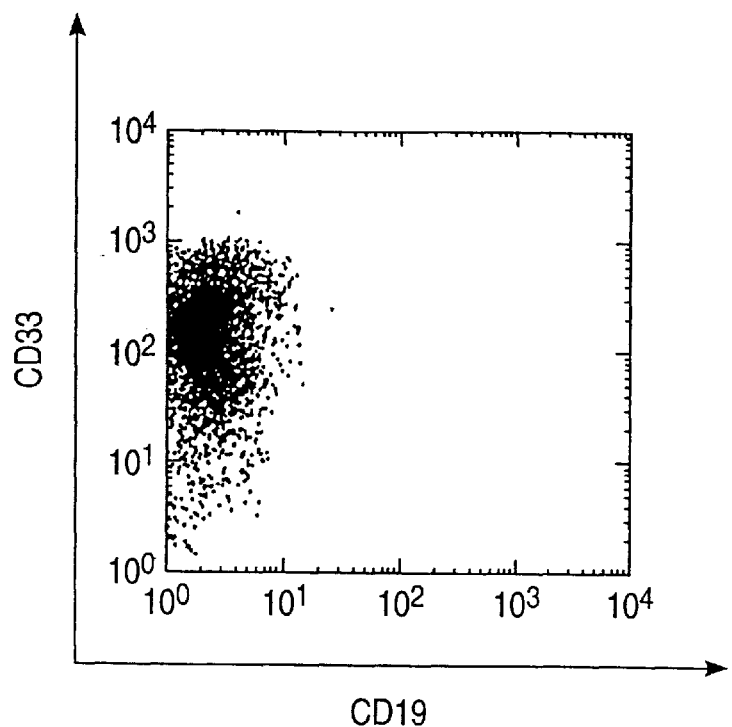
Figure 5F:
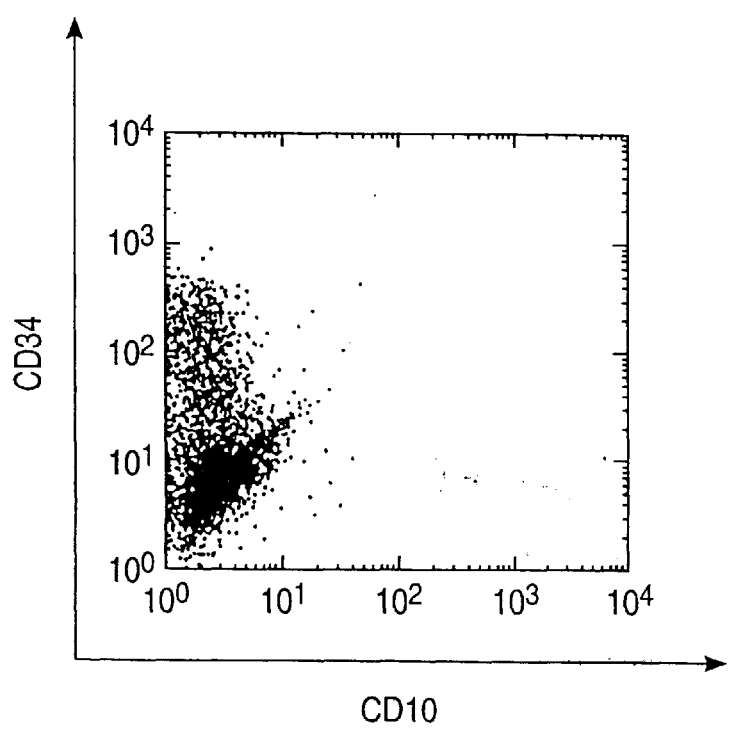

To refine our understanding of the downstream stages of hematopoietic stem cell differentiation, early B-cell precursors were examined for their T-cell reconstitution potential. It has been reported that the earliest B-cell precursor is identifiable by membrane expression of CD34 and of CD10 but absence of CD19 and CD2. Uckun (1990). The data presented herein confirm that there is a small subset of CD34$^+$Lin$^-$ (Lin includes among other markers CD19 and CD2) expressing CD10 (FIG. 4). These CD34$^+$Lin$^-$CD10$^+$ cells (hereafter referred to as 10$^+$) reside in the RA$^+$ population, because sorting for CD10$^+$ cells showed depletion of the RA$^+$ compartment approximately by half whereas it only reduced the RA$^-$ population by 10%. The clonogenic potential of 10$^+$ cells in the methylcellulose assay was almost nonexistent with no erythroid colonies and almost no myeloid colonies produced except for very few CFU-C which were composed of macrophages only (Table 5). Co-cultivation of 10$^+$ cells onto AC6.21 stroma in the presence of IL-3, IL-6 and LIF for 3 weeks showed only modest growth but strong differentiation into CD19$^+$ B cells (Table 5).

TABLE 5

Differentiative Potential of CD34$^+$Lin$^-$CD10$^+$Cells

|  | CFU per 1,000 cells | | | AC6.21 assay analysis | |
|---|---|---|---|---|---|
| Exp.# | CFU-C | BFU-E | CFU-mix | % CD33 | % CD19 |
| 1 | 2 | 0 | 0 | 83 | 8 |
| 2 | 2 | 0 | 0 | 17 | 61 |
| 3 | N.D. | N.D. | N.D. | 27 | 14 |

N.D. not done

One experiment demonstrated the presence of more than 60% CD19$^+$ B-cells in the bulk culture with cytokines after 3 weeks. Noticeably, these cultures also contained CD33$^+$ cells, although in much lower proportion than cultures initiated with RA$^+$ cells (see Table 4).

Myeloid and erythroid progenitor cells are virtually nonexistent in the CD34$^+$Lin$^-$CD10$^+$ cell population (Table 6). Methylcellulose cultures were established in the presence of human recombinant IL-3 (10 ng/ml) (Sandoz Pharma, Basel, Switzerland), granulocyte-monocyte colony stimulating factor (GM-CSF) (25 ng/ml), granulocyte CSF (G-CSF) (25 ng/ml), erythropoietin (EPO) (1.2 U/ml), and c-kit-:Ligand (KL) (10 ng/ml) (R&D systems, Minneapolis, Minn.). Cultures were incubated in humidified atmosphere at 37° C. 5% CO$_2$ 95% air for 2 weeks. Bone marrow co-cultures were established on pre-formed AC6.21 mouse bone marrow stroma in the presence of IL-3 (10 ng/ml), IL-6 (10 ng/ml) and LIF (50 ng/ml). After 3 weeks of culture, all cells were harvested and counted to calculate total cellular expansion. Cells were stained with fluorescein and PE-conjugated mAbs and analyzed on a fluorescence-activated cell scanner (Becton Dickinson). Specific cell staining was measured in the live cell gate as determined by size, granularity and propidium iodide exclusion. Results are expressed as % of positive cells after background subtraction (staining with irrelevant mouse IgG1 and IgG2a antibodies).

Occasional myeloid colony forming units (CFU) composed of large mononuclear cells were observed (2 per 1000 cells). The presence of such rare colonies due to sort contamination of $CD34^+Lin^-CD10^-$ cells seems unlikely since erythroid colonies were never detected. Highly purified $CD34^+Lin^-CD10^+$ cells obtained after two rounds of flow cytometry sorting yielded no such colony formation even after extended periods of culture (3 and 4 weeks). As anticipated, the $CD34^+Lin^-CD10^-$ population tested in parallel, generated a large number of colonies of either myeloid, erythroid or mixed (erythroid and myeloid) lineages (Table 6).

$CD34^+Lin^-CD10^+$ cells were also evaluated in stroma-supported bone marrow cultures. Sorted cells were co-cultivated on murine AC6.21 stromal cells in the presence of IL-3, IL-6 and leukemia inhibitory factor (LIF), a cytokine combination known to support the growth of adult hematopoietic cells as described by Murray et al. (1994). After 3 weeks, $CD34^+Lin^-CD10^-$ cells expanded considerably (174 to 500 fold total cellular expansion) and 3–18% $CD34^+$ cells were still present in the culture, indicating some retention of primitive hematopoietic cells. Morphologically heterogeneous populations of myeloid cells were observed. The great majority of cultured cells (86–97%) expressed the myeloid antigen CD33, with no detectable $CD19^+$ lymphoid cells.

In contrast, under identical experimental conditions, $CD34^+Lin^-CD10^+$ cells demonstrated a limited proliferative potential (3 to 42 fold total cellular expansion). Few $CD34^+$ cells (0.7 to 3%) were maintained in the culture and the cells showed strong potential to differentiate into $CD19^+$ lymphoid cells.

A preliminary experiment indicated that $CD34^+Lin^-CD10^+$ cells did not provide long-term (8 weeks) hematopoietic reconstitution of human bone fragments implanted into SCID mice. Also, the depletion of CD10 from the $CD34^+Lin^-$ population did not prevent hematopoietic repopulation of SCID-hu bones. Thus, $CD34^+Lin^-CD10^+$ cells are functionally and phenotypically distinct from stem cells.

The results obtained are presented in Table 6 where N.T. stands for not tested; results of methylcellulose cultures are expressed as numbers of myeloid (CFU-G, M and GM)/erythroid (BFU-E and CFU-E)/multipotent (CFU-mix) progenitors per 1000 cells plated. In Experiments 2 and 3, $CD10^-$ cells are also $CD45RA^-$, which explains their higher CFU-mix content. In Experiments 4 and 5, $CD10^+$ cells were highly purified after two consecutive rounds of flow cytometry sorting. Reanalysis of sort purity after the first round was 91% and 98% for Experiments 4 and 5, respectively.

EXAMPLE 4

B Lymphoid Potential of $CD34^+$ CD45RA Subsets

The capacity to differentiate into B-cells was analyzed after co-culture on AC6.21 murine bone marrow stromal cells known to support human B-cell differentiation from fetal and adult bone marrow $CD34^+Lin^-$ cells. Baum et al. (1992); and DiGiusto et al. (1994). As described above, $RA^+$ and $RA^-$ cells grew on AC6.21 cells in the presence of IL-3, IL-6 and LIF. Cultures derived from $RA^+$ and $RA^-$ cells were almost exclusively composed of $CD33^+$ myeloid cells (Table 4).

A small but significant proportion of $CD19^+$ cells (1 to 2%) was often observed in the $RA^+$ cultures but not in the $RA^-$ culture. The forward and side scatter characteristics of the CD19+cells were consistent with their B-cell nature, and $RA^+$ cultures also contained $CD10^+$ cells. Under these experimental conditions, B-cell production from the $RA^-$ cultures was not detected even after omitting IL-3 to reduce the proliferation of myeloid cells. The lack of $CD19^+$ B-cell production in $RA^-$ cultures may be due to a slow kinetic of differentiation. Indeed, there is an early B-cell progenitor in the $RA^-$ subset because, as mentioned earlier, this subset was capable of engraftment in SCID-hu bones with sustained production of donor-derived B-cells (FIG. 3). In contrast, $RA^+$ cells seem to contain a later B-cell progenitor, readily differentiated and expanded in vitro but incapable of long-term repopulation of bone marrow.

Considerable B lymphoid differentiation was observed in IL-3, IL-6, and LIF stimulated bone marrow cultures initiated with $CD34^+Lin^-CD10^+$ cells (Table 6). After 3 weeks, such cultures contained 8–76% $CD19^+$ B cells which otherwise lacked CD34, expressed CD10 and had the characteristics (size and granularity) of lymphoid cells (Table 6 and FIG. 5). These data confirm that $CD34^+Lin^-CD10^+$ ABM cells are capable of serving as B cell precursors and indicate that their B cell progenitor potential is more immediate than that of their $CD10^-$ counterpart.

EXAMPLE 5

T Lymphoid Potential of CD45RA Subsets

1. SCID-hu thymus assay.

HLA immunophenotyping of the recipient thymus and of donor ABM cells was performed as described above. Fragments of fetal thymi were placed on nitrocellulose filters (0.8 Am, Costar Corp., Cambridge, Mass.) on top of gelatin rafts (Gelfoam, Upjohn) according to the method described by Galy et al. (1993). After 7–13 days of incubation at 25° C. and 5% $CO_2$, thymus fragments were irradiated with 250

TABLE 6

Myeloid, Erythroid and Lymphoid Progenitor Cells in $CD34^+Lin^-CD10$ Cell Subsets ($CD10^+$ and $CD10^-$)

| | Myelo-Erythroid Clonogenic Progenitors | | Fold Cellular Expansion | | Bone Marrow Culture Analysis | | | | | |
|---|---|---|---|---|---|---|---|---|---|---|
| | | | | | % $CD34^+$ cells | | % $CD33^+$ cells | | % $CD19^+$ cells | |
| Experiment # | $CD10^+$ | $CD10^-$ | $CD10^+$ | $CD10^-$ | $CD10^+$ | $CD10^-$ | $CD10^+$ | $CD10^-$ | $CD10^+$ | $CD10^-$ |
| 1 | N.T. | N.T. | N.T. | N.T. | N.T. | 2.6 | 26 | 96 | 14 | 0 |
| 2 | 2/0/0 | 49/58/6.6 | 42 | 200 | 3 | 5 | 83 | 97 | 8 | 0 |
| 3 | 2/0/0 | 29/78/6 | 18 | 500 | 0.7 | 18.3 | 16 | 91 | 61 | 0 |
| 4 | 0/0/0 | 22/38/1 | 24 | 174 | 0.2 | 8.5 | 55 | 86 | 27 | 0.5 |
| 5 | 0/0/0 | 49/49/2.5 | 3.2 | 203 | N.T. | 3 | 7 | 93 | 76 | 0 | cGy from a $^{137}$Cs source (J.L. Shepherd & Associates), washed and immediately micro-injected with the HLA-mismatched sorted cells in a 1 μl volume using an oil-filled micro-injector (Narishige) and 1 mm diameter glass micropipettes (World Precision Instruments). Fragments were placed back on the filters and incubated at 37° C., 5% $CO_2$ overnight and then inserted under the kidney capsule of anesthetized 6–8 week old SCID mice bred in our facilities. Mice were sacrificed 6 to 7 weeks after transplantation and the thymus grafts were recovered, reduced to a single cell suspension, and subjected to three-color immunofluorescence analysis on the FACScan. The following MAbs were used: FITC anti-HLA antibodies, -CD2 or mouse IgG1 irrelevant control, PE W6/32, anti-CD1a (Coulter), anti-CD4 or mouse IgG1 control (Becton Dickinson) and Tri-color (TC)-conjugated anti-CD45, -CD8, -CD3 or mouse IgG1 irrelevant control (Caltag).

Figure 6:
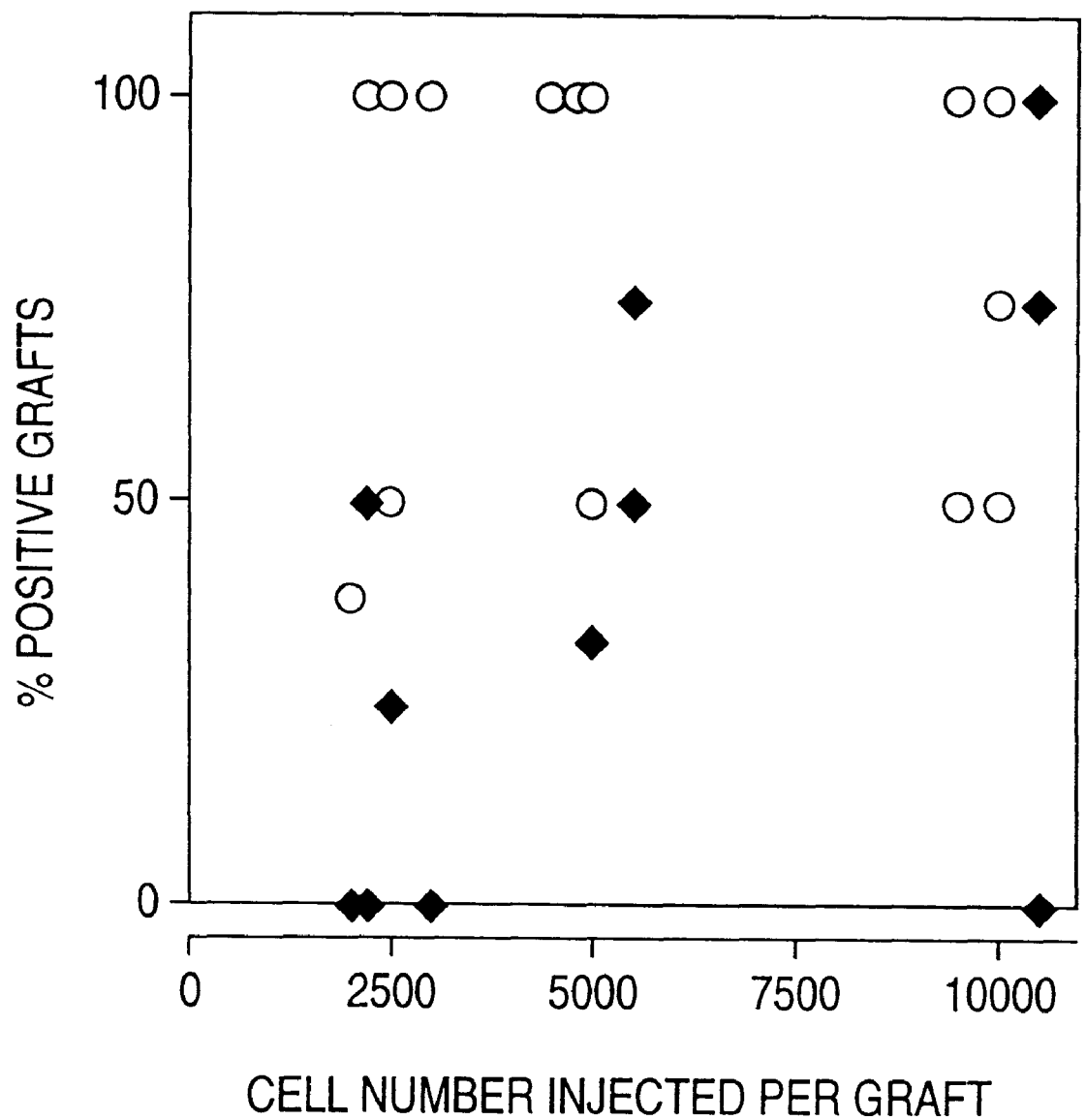
FIG. 6: T-cell reconstitution in SCID-hu thymus assay. Each dot represents one thymus graft, analyzed 7 weeks after injection of varying numbers of CD34$^+$Lin$^-$CD45RA$^+$ (open circles) or CD34$^+$Lin$^-$CD45RA$^-$ (closed diamonds) cells.
Figure 7A:
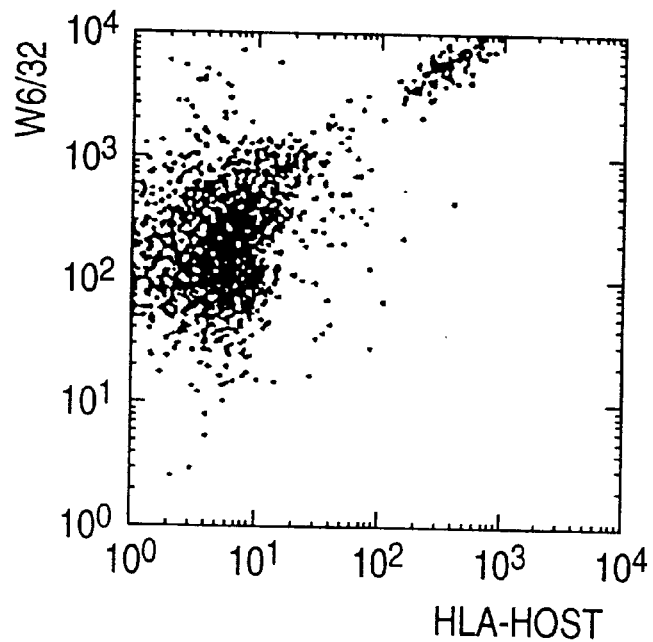
FIG. 7A through FIG. 7D: Phenotypic analysis of a SCID-hu thymus graft reconstituted with CD34$^+$Lin$^-$CD10$^+$ cells. This representative graft was analyzed 6 weeks after injection of 9,000 CD34$^+$Lin$^-$CD10$^+$ cells.
Figure 7B:
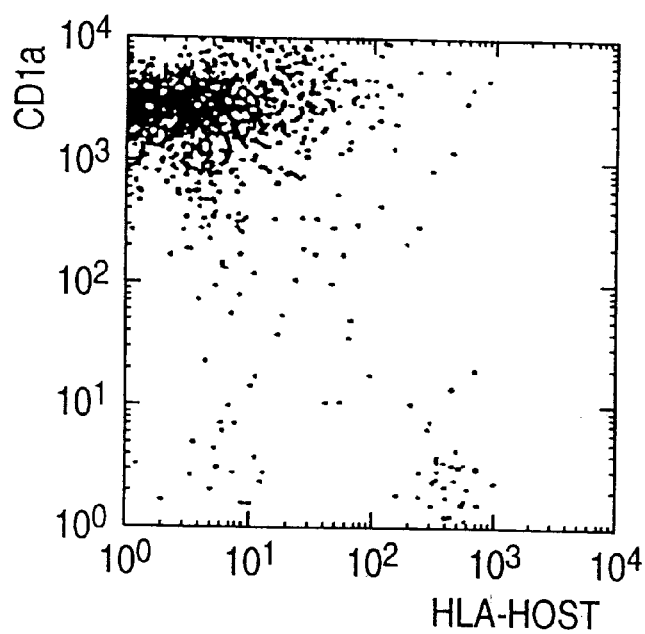
Figure 7C:
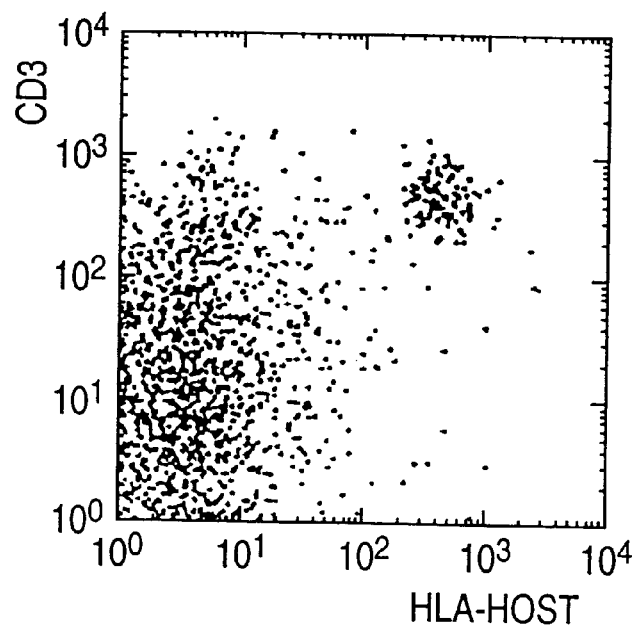
Figure 7D:
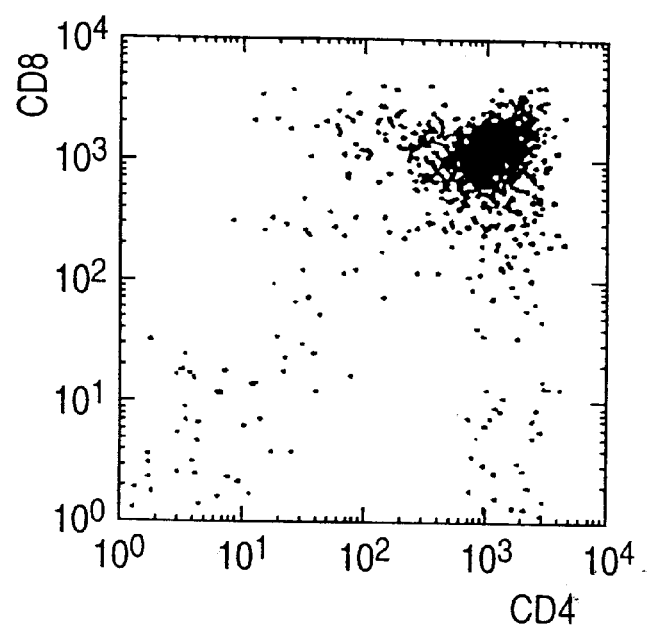

The T progenitor cell potential was tested in the SCID-hu thymus assay, which has been shown to support intrathymic T-cell differentiation of CD34$^+$Lin$^-$ cells isolated from fetal and adult bone marrow as well as from adult mobilized peripheral blood. DiGiusto et al. (1994); and Galy et al. (1994). Decreasing cell numbers of either RA$^+$ or RA$^-$ subsets were injected into thymic grafts which were etrieved and analyzed 6 to 7 weeks post-transplantation into SCID mice. Both subsets engrafted and generated T-cells; however, it was clear that the RA$^+$ subset consistently engrafted more successfully, particularly at low cell numbers (2 to 3000 cells per graft) (FIG. 6). The quality of donor-derived thymopoiesis was examined in each graft by 3-color immunostaining. Both RA$^+$ and RA$^-$ subsets gave rise to donor-thymocytes which for the most part expressed high levels of CD1, co-expressed CD4 and CD8 and had a graded expression of CD3. Mature T-cells bearing the αβ or γδ TCR could be expanded from thymic grafts reconstituted with RA$^+$ cells as described. Galy et al. (1994).

Thymic maturation is associated with increase of CD3, loss of CD1 and of the co-expression of CD4 and CD8 antigens. Galy et al. (1993); and Terstappen et al. (1992). Careful examination of these parameters showed no significant difference in the phenotype of thymocytes generated from RA$^+$ or RA$^-$ subsets. Therefore, the SCID-hu thymus assay, as currently designed, did not allow us to distinguish between early and late T-progenitor cells within the time frame examined (6 to 7 weeks post injection). Taken together, these data indicate that RA$^+$ cells contain late progenitors for the myeloid and B lineages, and display vigorous T-progenitor cell activity. The RA$^-$ subset has primitive potential for the erythroid, myeloid and B-cell lineages and also contains T progenitor cell activity although at a reduced frequency compared to RA$^+$ cells.

2. Expression of Thy-1, CD38 or HLA-DR and T progenitor cell activity.

One practical consequence of these results is that the presence of T-progenitor cell activity can be deduced from the phenotypic analysis presented in FIG. 2. Because RA$^+$ cells have T progenitor cell activity and at the same time are almost entirely positive for CD38 and HLA-DR, it can be logically deduced that the activity should be retrieved in the CD38+or HLA-DR$^+$ compartments. The results verifying this are shown in Table 7. In Table 7, engraftment success is expressed as the ratio of grafts positive for donor cells (>1%) to the number of grafts analyzed.

TABLE 7

| Subsets | experiments | cell tested | engraftment success |
|---|---|---|---|
| CD34$^+$Lin$^-$CD38$^+$ | 1 | 10,000 | 4/4 |
| CD34$^+$CD15$^-$ HLA-DR$^+$ | 1 | 10,000 | 3/6 |
| CD34$^+$Lin$^-$Thy-1$^+$ | 3 | 10,000 | 16/20 |
| CD34$^+$Lin$^-$Thy-1$^-$ | 3 | 10,000 | 10/20 |
| CD34$^+$Lin$^-$CD45RA$^+$ Thy-1$^-$ | 2 | 2,000 | 7/8 |
| CD34$^+$Lin$^-$CD45RA$^-$ Thy-1$^+$ | 2 | 2,000 | 7/8 |

Thy-1 is a marker expressed on very primitive hematopoietic cells in fetal and adult bone marrow, and umbilical cord blood. Baum et al. (1992); Craig et al. (1994); and Mayani and Lansdorp (1994). Both CD34$^+$Lin$^-$Thy-1$^+$ and CD34$^+$Lin$^-$Thy-1$^-$ ABM cells could generate T-cells. The phenotypic profile shown in FIG. 2 indicates that the T-cell reconstitution potential of Thy-1 cells might be due to the presence of RA$^+$ cells. To test this hypothesis sorted CD34$^+$Lin$^-$CD45RA$^+$Thy-1$^-$ cells were assayed in the SCID-hu thymus system, and displayed good T-cell reconstitution potential even when low cell numbers were used (Table 7). The T-cell reconstitution activity of the small subset of cells bearing CD45RA and Thy-1 has not been tested. On the other hand, CD34$^+$Lin$^-$CD45RA$^-$Thy-1$^+$ cells display good T-cell reconstitution potential. These cells are also very strongly enriched in primitive hematopoietic activity as shown by maintenance of CD34$^+$Lin$^-$ and CD34$^{+CD}$45RA$^-$ cells in culture with CFU-mix and BFU-E secondary clonogenic potential (Table 3). With all the subsets examined (Thy-1$^+$, Thy-1$^-$, CD38$^+$, HLA-DR$^+$) thymopoiesis was qualitatively equivalent to that generated from RA$^+$ cells in terms of CD1, CD3, CD4 and CD8 expression after 6 weeks.

When 10$^+$ cells were injected into thymus fragments, T-cell reconstitution was observed even when low cell numbers were tested (2,000 cells). After 6 weeks, donor-derived thymocytes co-expressed CD4 and CD8 with high CD1a and graded expression of CD3, as seen with thymocytes derived from other subsets (FIG. 7). This 10$^+$ population seems therefore mostly committed to the lymphoid lineages.

In the SCID-hu thymus assay T-cell potential was found in the RA$^-$, RA$^+$ and 10$^+$ subsets. As mentioned above, the hierarchical relationship between RA$^-$, RA$^+$ and 10$^+$ cells could not be inferred from qualitative differences in the T-cell progeny because at 6 weeks, the reconstituted thymus grafts had comparable proportions of CD1, CD3 and CD4/CD8 double positive cells in the donor-derived compartment.

Figure 8A:
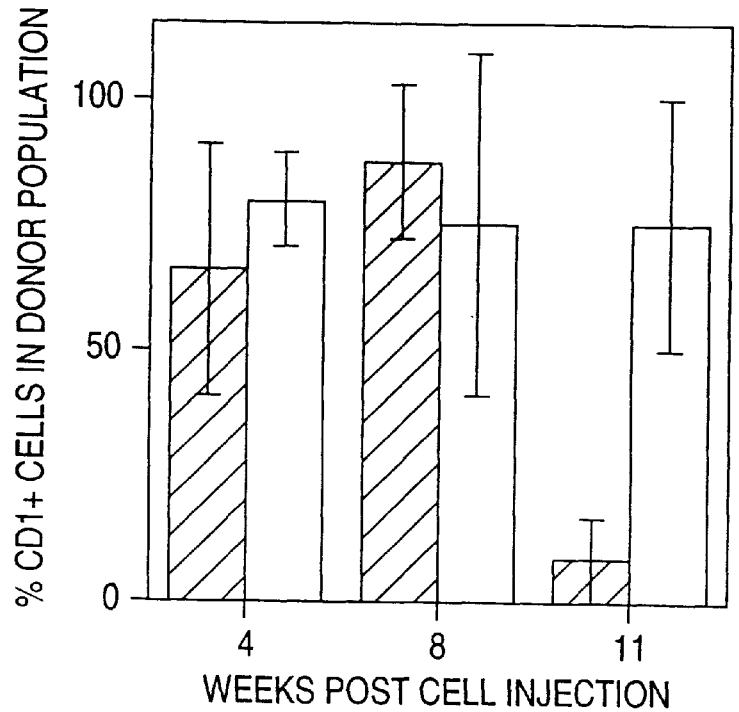
FIG. 8A through FIG. 8B: Qualitative assessment of thymocyte reconstitution in the SCID-hu thymus assay over time. At 4, 8 and 11 weeks post-cell injection of 2,000 CD34$^+$Lin$^-$CD10$^+$ cells (shaded bars) and of 10,000 CD34$^+$Lin$^-$CD10$^-$ cells (open bars). Thymocytes were analyzed by three-color immunostaining for the presence of donor cells and expression of CD1a and CD3. Results are expressed as the % of donor cells expressing CD1a (FIG. 8A) or CD3 (FIG. 8B) ±SD (n=4 grafts at each time point for each group).
Figure 8B:
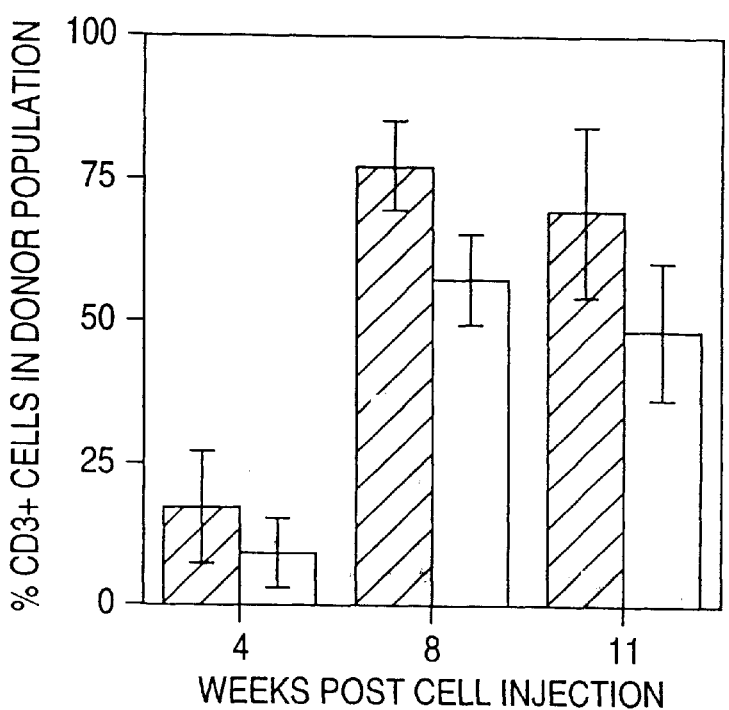
Figure 9A:
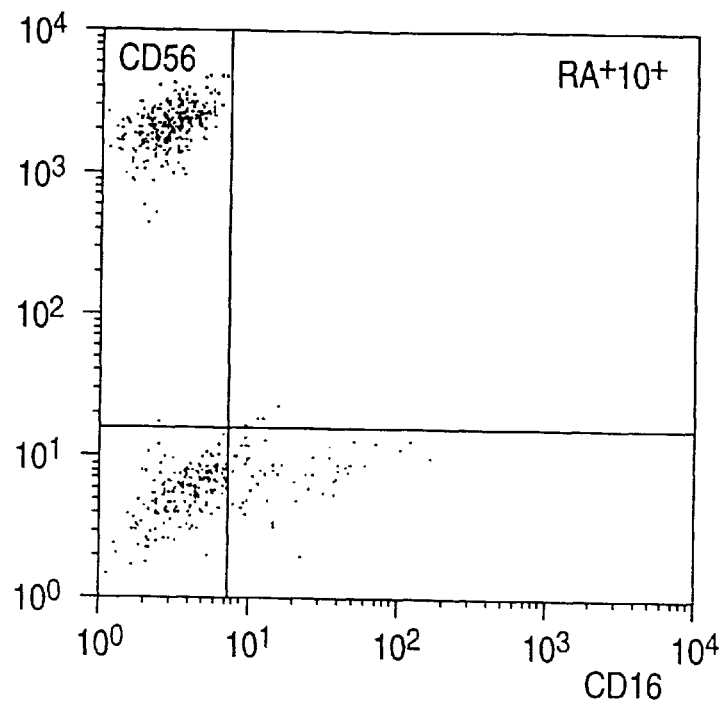
FIG. 9A through FIG. 9D: A representative phenotypic analysis of AC6.21 cultures initiated by CD34$^+$Lin$^-$CD45RA$^+$ or CD34$^+$Lin$^-$CD45RA$^-$ cells in the presence of IL-2.
Figure 9B:
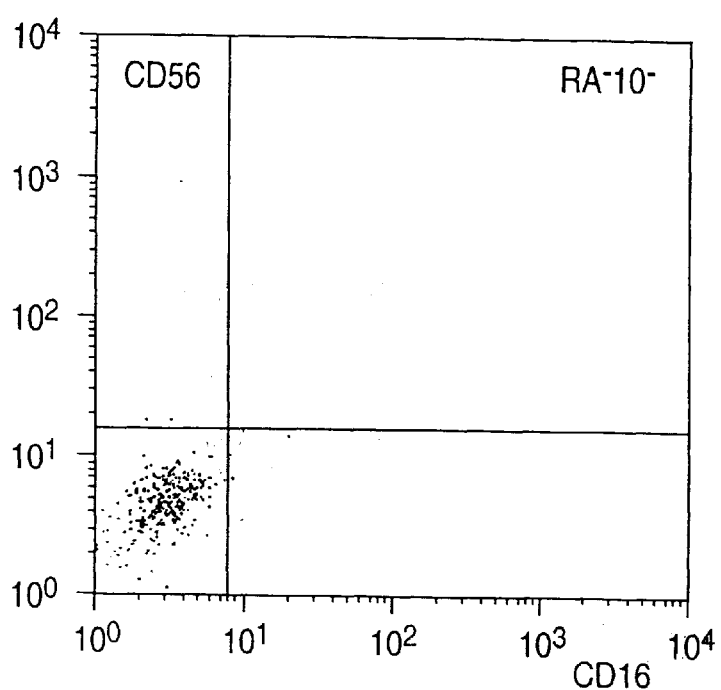
Figure 9C:
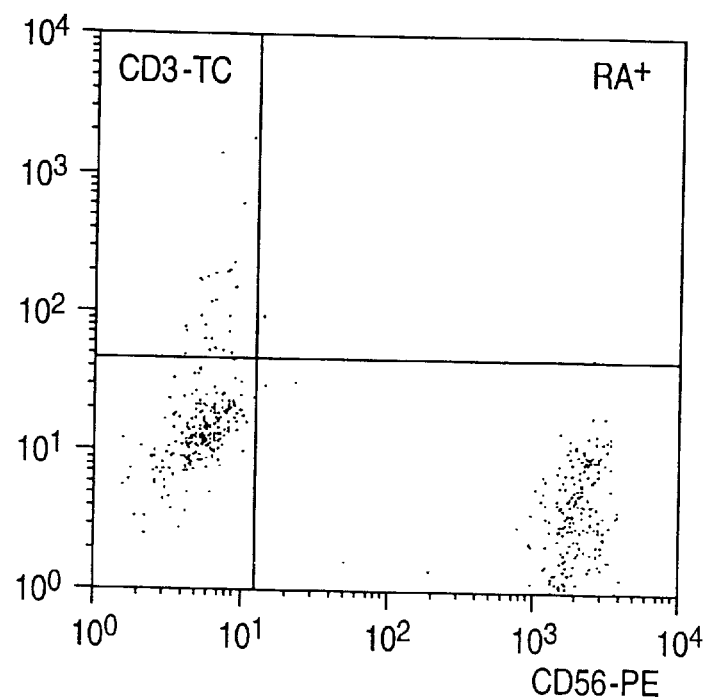
Figure 9D:
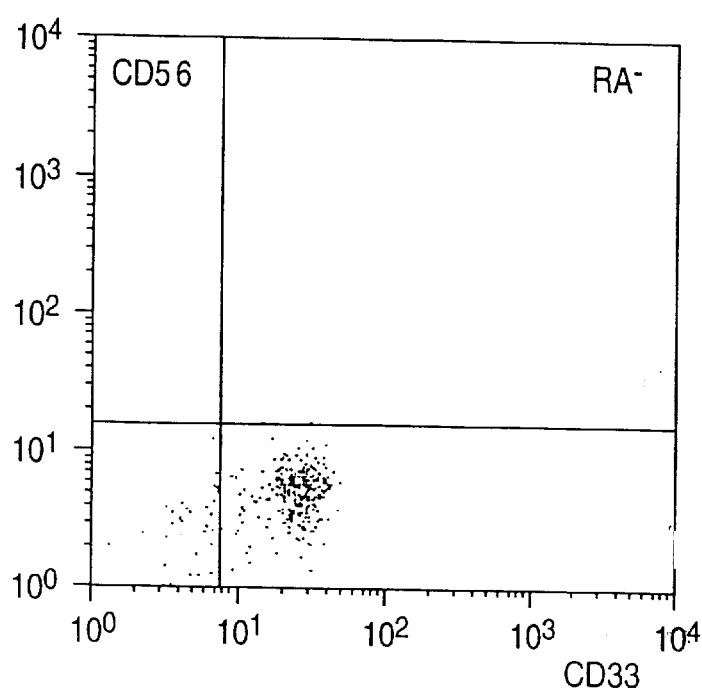

Kinetics studies were undertaken to examine the T-cell reconstituting potential of 10$^+$ cells and CD34$^+$Lin$^-$CD10$^-$ (10$^-$) cells. It was found that both 10$^+$ and 10$^-$ cells could repopulate thymic grafts and generate immature thymocytes (expressing high levels of CD1a) up to 8 weeks post cell injection. Between 8 and 11 weeks of reconstitution, however, it seems that the grafts injected with 10$^+$ cells ceased to produce immature T cells and only contained phenotypically mature thymocytes (CD1$^-$, CD4$^+$ or CD8$^+$ and CD3$^{bright}$) (FIG. 8).

Taken together, these data strongly indicate that 10$^+$ cells are the most mature and are strongly committed to lymphoid differentiation.

EXAMPLE 6

NK Progenitor Cell Potential of CD45RA Subsets

It has recently been demonstrated that NK cells can be differentiated from CD34$^+$ bone marrow cells with IL-2 and stroma. Miller et al. (1992) Blood 80:2182–2187; and Lotzova et al. (1993) J. Immunol. 150:5263–5269. The ability of the murine stromal cell line AC6.21 to support NK cell differentiation was examined. Cells sorted into CD34$^+$Lin$^-$ subsets, as described in Example 1, were assayed for NK cell differentiation as follows.

In vitro co-culture on AC6.21 cells for NK-cell differentiation.

For NK cell assays, sorted cells were plated onto preformed AC6.21 monolayers in IMDM with 10% FCS, 40 μg/ml transferrin (Boehringer Mannheim), 5 μg/ml insulin (Sigma) supplemented with 50 ng/ml recombinant human IL-2 (Sandoz Pharma, Basel Switzerland). After 1 week, half of the medium was replaced by medium containing rhIL-2 (50 ng/ml). Subsequently, medium containing IL-2 was changed twice a week for at least two weeks to supplement for the disappearance of stromal cells. Cells were harvested by pipetting, counted and immunostained with PE-conjugated anti-CD56 and FITC conjugated anti-CD3 MABs or their appropriate negative controls (Becton Dickinson). Cells were analyzed on a FACScan fluorescent cell analyzer (Becton Dickinson).

Figure 10A:
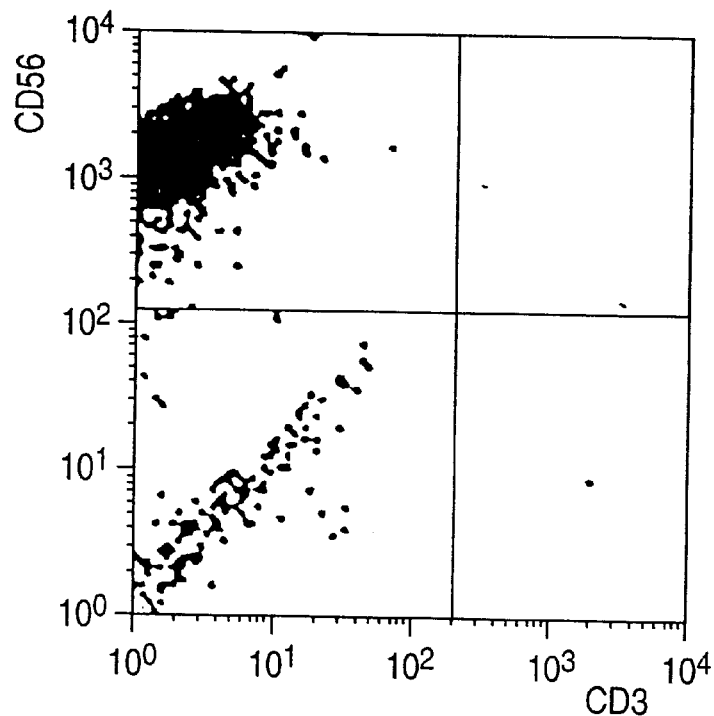
FIG. 10A through FIG. 10B: The phenotypic analysis of a AC6.21 culture initiated with CD34$^+$Lin$^-$CD10$^+$ cells in the presence of IL-2 at week 4.
Figure 10B:
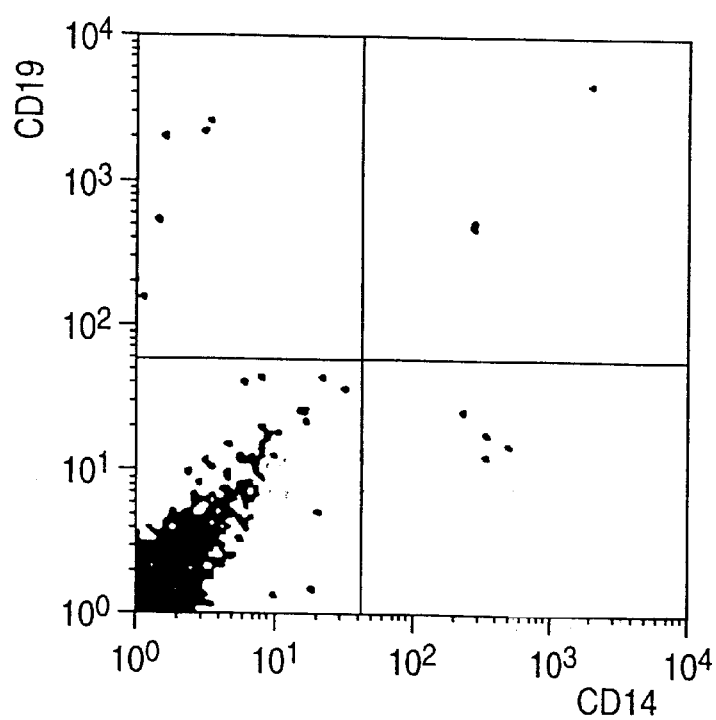
Figure 11A:
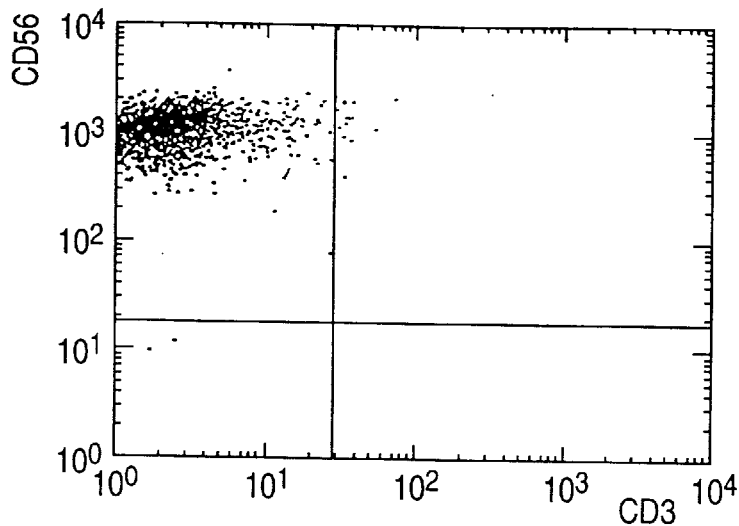
FIG. 11A through FIG. 11C.
Figure 11B:
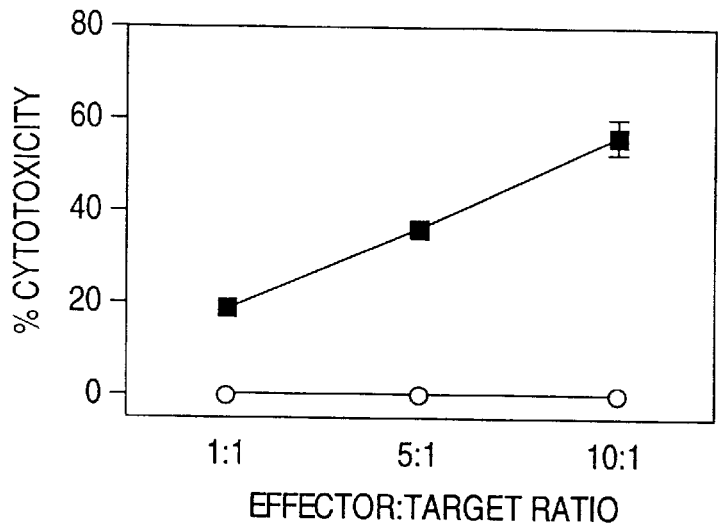
Figure 11C:
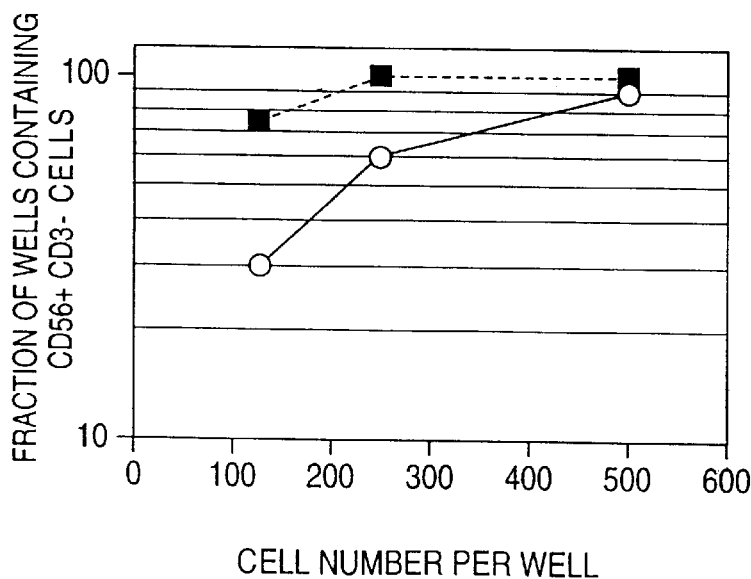
Figure 12A:
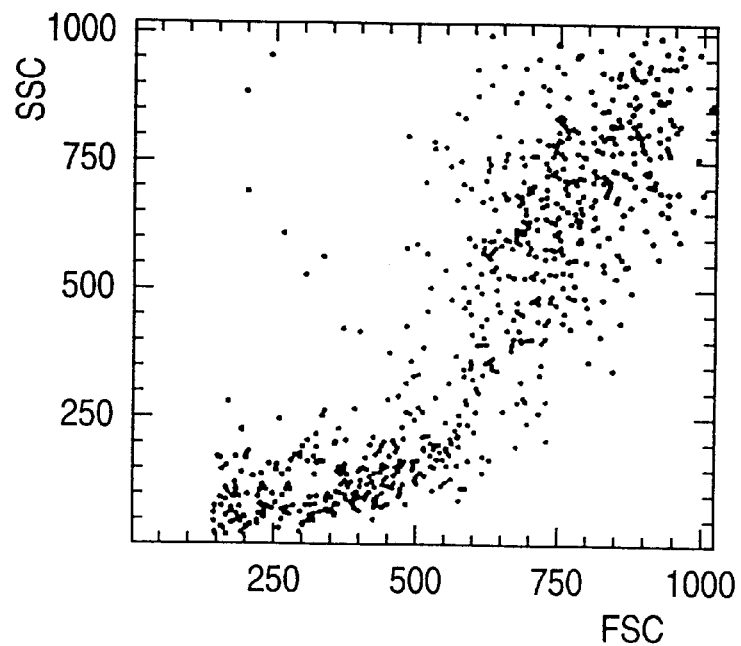
FIG. 12A through FIG. 12H: Representative example of flow cytometry and immunostaining analyses of cultures initiated with CD34$^+$Lin$^-$CD10$^+$ ABM cells (FIGS. 12A–12D) and CD34$^+$Lin$^-$CD10$^-$ ABM cells (FIGS. 12E–12H). Two-color staining was performed to identify CD1a, HLA-DR, CD14 and CD15 expression on live cells excluding propidium iodide.
Figure 12B:
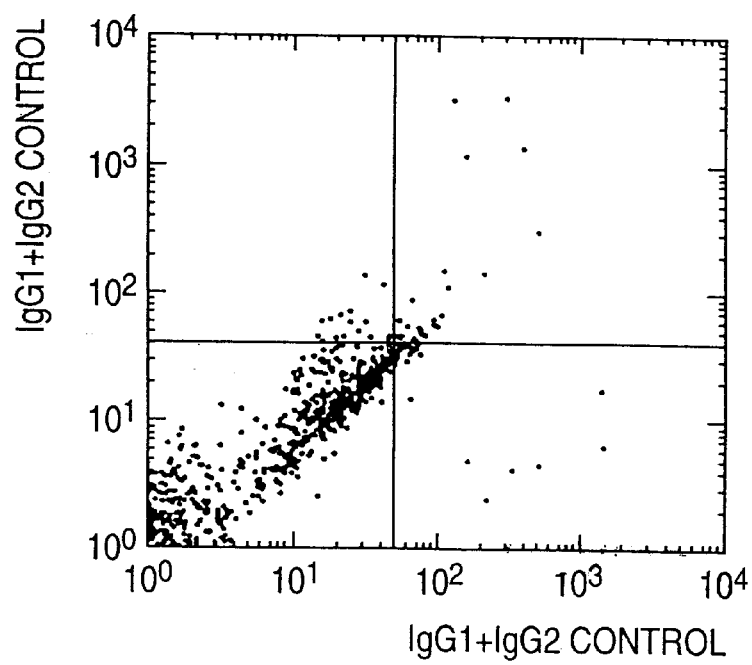
Figure 12C:
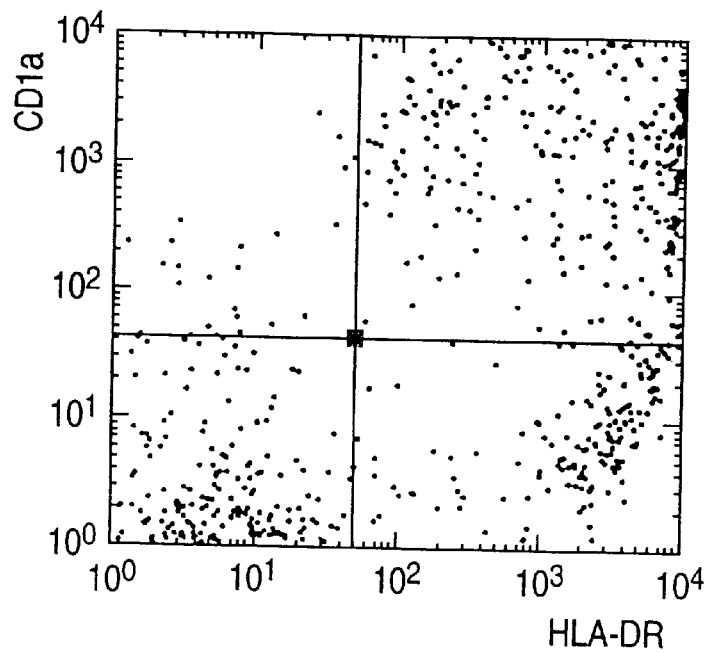
Figure 12D:
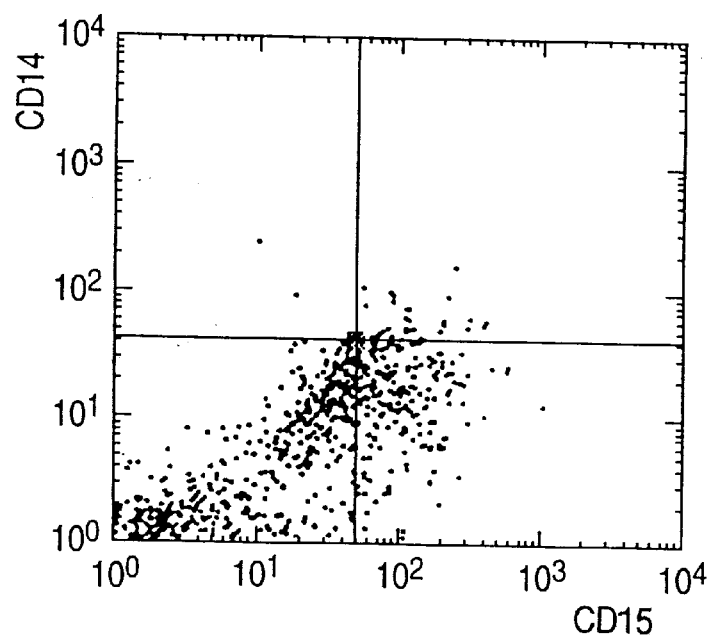
Figure 12E:
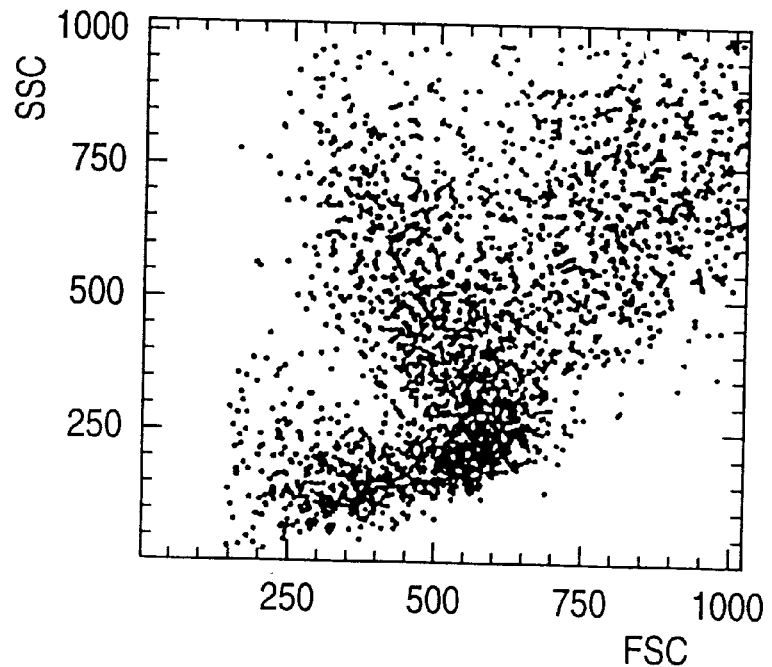
Figure 12F:
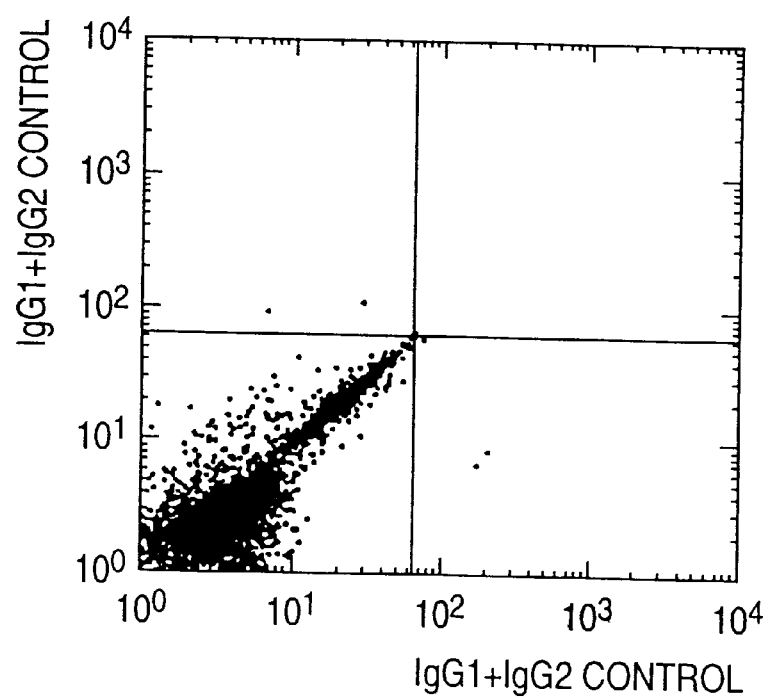
Figure 12G:
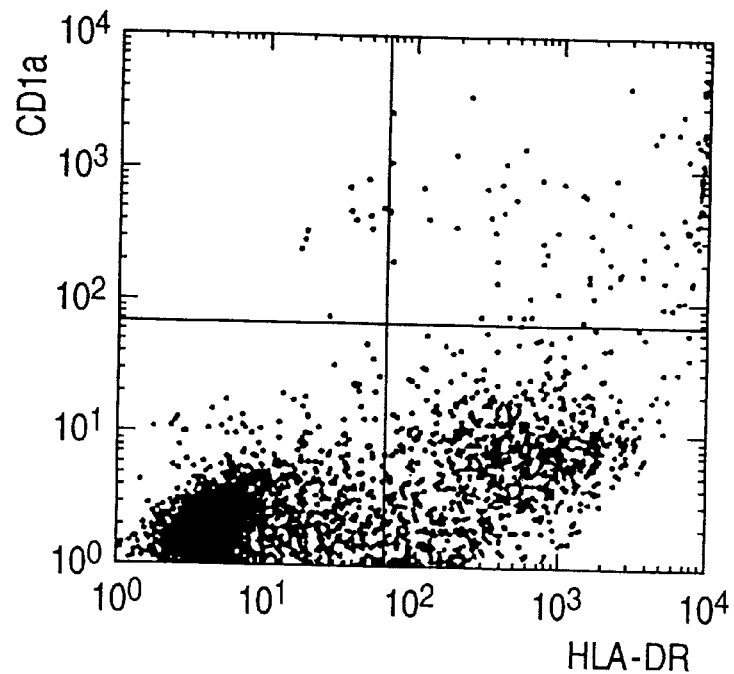
Figure 12H:
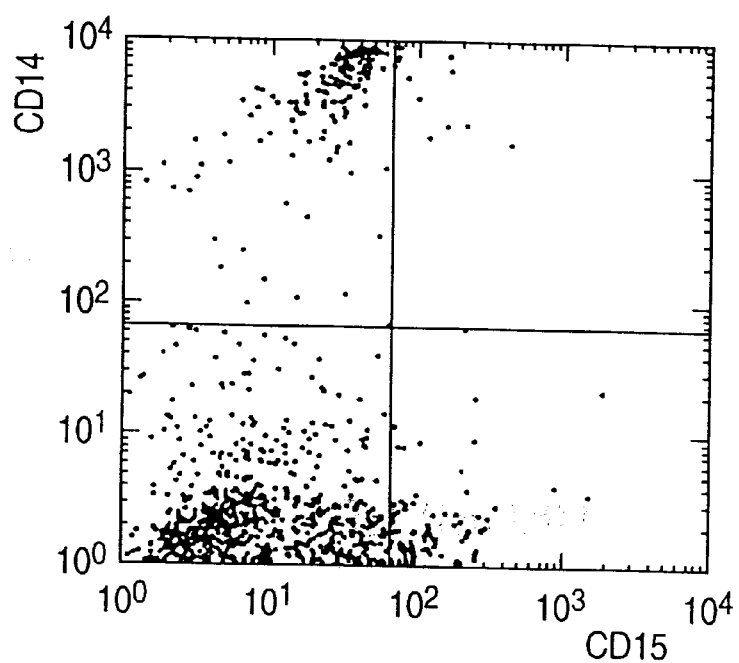

Under these conditions, within 2 too 3 weeks, RA$^+$ cells developed into lymphoblasts expressing CD56 but not CD3 (FIGS. 9 and 10). Positivity for CD56 and lack of detectable surface CD3 expression is typical of NK cells. Lanier et al. (1992) Immunology Today 13:392–395. RA$^+$ cultures generally destroyed their supportive stromal layer within the first two weeks as described by Miller et al. (1992). Furthermore, the 10$^+$ subset, which has almost no myeloid potential but has T and B-cell progenitor activity described Example 2, can generate NK cells (FIG. 11). The CD56+ CD3$^-$ NK cells produced in the culture also destroyed the stroma.

The RA$^-$ subset, however, did not give rise to NK cells very efficiently within the time period examined (up to 7 weeks). At 3 weeks, the cultures contained a large proportion (>90%) of CD33$^+$ myeloid cells which did not expand very well past 6 weeks. A few NK cells could sometimes be seen in the RA$^-$ culture, but their proportion was always very low compared to RA$^+$10$^-$ and 10$^+$ cultures.

Limiting dilution experiments were carried out to estimate the frequency of cells responsive in this assay. Growing wells were scored visually at week 6 for the presence of lymphoblastic cells and scoring was confirmed by immunostaining for cells expressing CD56 but not CD3 (Table 8).

TABLE 8

Week 6 NK Culture

|  | cells/well | NK positive |
|---|---|---|
| CD10$^+$ (RA$^+$) | 500 | 4/6 |
| RA$^+$10$^-$ | 2 | 2/96 |
|  | 10 | 1/47 |
|  | 50 | 0/26 |
|  | 100 | 3/24 |
| RA$^-$10$^-$ | 5000 | 3/12 |
|  | 1000 | 0/24 |
|  | 150 | 0/24 |
|  | 10 | 0/36 |

In three independent experiments RA$^+$ (10$^+$ and 10$^-$) cells were shown to generate NK cells whereas RA$^-$ cells do so much less efficiently. Differentiation of NK cells in this system was confirmed since the starting RA$^+$ population did not express CD56. Also, the high frequency of NK progenitors in the RA$^+$ population does not seem compatible with expansion of mature cells given the purity of the sorts upon reanalysis (>90%). Furthermore, the RA$^+$10$^-$ cells have been through two rounds of sorting against lineage positive cells devoid of CD56$^+$ mature NK cells. The lower frequency of NK progenitors in the RA$^-$ subset is likely to be due to its immaturity as well as masking by the high proportion of cells not committed to the lymphoid lineage. To confirm this hypothesis, 3 week-old AC6.21 co-cultures initiated with RA$^-$ cells were immunostained with anti-CD34 plus anti-CD45RA antibodies and cultured cells were sorted into CD34$^+$Lin$^-$CD45RA$^-$ and CD34$^+$Lin$^-$CD45RA$^+$ subsets. The enrichment in BFU-E and CFU-mix activities was confined to the sorted CD34$^+$CD45RA$^-$ cells and again, NK cells were generated predominantly from the sorted CD34$^+$CD45RA$^+$ progeny.

These results indicate a good correlation between maintenance of phenotype and function. This supports the fact that RA$^-$ cells are more immature and are the immediate precursors or RA$^+$ cell subsets.

Differentiation of ABM CD34$^+$Lin$^-$CD10$^+$ cells into CD34$^-$CD56$^+$CD3$^-$ NK cells was obtained within 1 to 2 weeks of culture on the murine bone marrow stromal cell line AC6.21 in the presence of IL-2 in all experiments performed (n=6). NK differentiation potential of CD34$^+$Lin$^-$CD10$^+$ cells was confirmed with highly purified cells obtained after two consecutive rounds of flow cytometric sorting.

No monocytic/myeloid cells were observed in CD34$^+$Lin$^-$CD10$^+$ cultures although such culture conditions support the generation of monocytic/myeloid cells in cultures of CD34$^+$Lin$^-$CD10$^-$ cells. The CD56+CD3$^-$ NK cells derived from CD34$^+$Lin$^-$CD10$^+$ cells (FIG. 11-Panel A) were functional as demonstrated by dose-dependent killing of NK-sensitive K562 target cells according to the method described by Sanchez et al. (1994) J. Exp. Med. 180:569 (FIG. 11-Panel B). By limit dilution analysis, according to the method described by Taswell (1981) J. Immunol. 126:1614, of one ABM sample, a higher frequency of NK progenitors was obtained with CD34$^+$Lin$^-$CD10$^+$ cells (1/75) compared to CD34$^+$Lin$^-$CD10$^-$ $^{cells}$ (1/325) (FIG. 11-Panel C). Kinetic studies indicate that CD56+CD3$^-$ NK cells appeared earlier in cultures initiated with CD34$^+$Lin$^-$CD10$^+$ cells (phenotypically detectable in the culture at day 9) than in cultures of CD34$^+$Lin$^-$CD10$^-$ (not phenotypically detectable in the culture before day 16). Thus, CD34$^+$Lin$^-$CD10$^+$ cells have a greater ability to generate NK cells than the rest of CD34$^+$Lin$^-$ ABM cells.

In conclusion, we present two novel findings with respect to NK cells. First, we show that AC6.21, a murine cell line, can support the differentiation of NK cells from human adult bone marrow in the presence of IL-2 Second, the small population of CD34$^+$Lin$^-$CD10$^+$ cells has NK differentiation potential in addition to B an T-cell progenitor activity, but is virtually devoid of myeloid activity. This is consistent with that population being a pre-thymic lymphoid progenitor.

EXAMPLE 7

Hierarchy of Lymphoid Progenitor Potential

The results presented here show clearly that RA$^-$ cells are more immature than RA$^+$ cells in the B, myeloid and erythroid lineages, and that RA$^+$ cells directly come from RA$^-$ cells. The relationship between the 10$^+$ and RA$^+$ subsets was then examined to derive a hierarchical model of lymphoid development. Three subsets, CD34$^+$Lin$^-$CD10$^+$, CD34$^+$Lin$^-$CD10$^-$CD45RA$^+$, and CD34$^+$Lin$^-$CD10$^-$ CD45RA⁻, were obtained after two consecutive sorts and tested in the B- and T-cell differentiation assays. As expected, $RA^-CD10^-$ cells did not produce detectable CD19+B-cells after three weeks of culture with AC6.21 cells and IL-3, IL-6 and LIF.

On the other hand, $CD10^+$ as well as $RA^+ CD10^-$ cells differentiated into $CD19^+$ and $CD10^+$ B cells (FIG. 5). In addition, it was observed that the $RA^+CD10^-$ cultures generated a small subset of $CD34^+CD10^+$ cells, therefore demonstrating the direct relationship between these two subsets.

tures of $CD10^+$ and $CD10^-$ cells from the same experiment. In Table 9, N/A stands for not applicable and NT stands for not tested.

TABLE 9

Immunophenotypic Analysis of Cultures Initiated with $CD34^+Lin^-CD10$ Subsets ($CD10^+$ and $CD10^-$)

| Experiment # | Length culture days | Starting population | Cellular expansion Fold | HLA-DR % | HLA-DR mfi | CD1a % | CD1a mfi | CD14 % | CD14 mfi | CD15 % | CD15 mfi |
|---|---|---|---|---|---|---|---|---|---|---|---|
| 1 | 12 | CD10⁺ | 9.5 | 40 | 3770 | 26 | 2067 | 0 | N/A | 26 | 120 |
|   |    | CD10⁻ | 95  | 27 | 470  | 2  | 757  | 24 | 5240 | 30 | 297 |
| 2 | 15 | CD10⁺ | 12  | 63 | 3885 | 42 | 2371 | 0  | N/A  | 18 | 127 |
|   |    | CD10⁻ | 60  | 32 | 817  | 2  | 852  | 20 | 4123 | 20 | 91  |
| 3 | 20 | CD10⁺ | N.T.| 55 | 2027 | 23 | 1520 | 0  | N/A  | N.T.| N.T.|
|   |    | CD10⁻ | N.T.| 51 | 546  | 0  | N/A  | 19 | 4090 | N.T.| N.T.|

EXAMPLE 8

Determining the Presence of Dendritic Cell Precursors

In the previous examples larger cells expressing CD33 were always observed, even in bone marrow cultures initiated with highly purified $CD34^+Lin^-CD10^+$ cells completely devoid of clonogenic progenitor cells (Table 9). However, in all experiments, the proportion of $CD33^+$ cells was considerably smaller than in cultures of $CD34^+Lin^-CD10^-$ cells. To fully explore the differertiative potential of $CD34^+Lin^-CD10^+$ cells, liquid cultures were initiated with 9 cytokines (IL-1, IL-3, IL-6, IL-7, KL, GM-CSF, tumor necrosis factor (TNF), FLT3/FLK2-ligand (FL) and EPO) in order to support the development of a broad spectrum of hematopoietic cells. ABM $CD34^+Lin^-CD10$ ($CD10^+$ and $CD10^-$) cell subsets were incubated at 2,000 cells per well in round bottom 96-well plates in IMDM medium supplemented with human recombinant IL-3, IL-6, GM-CSF (each at 25 ng/ml) (Sandoz Pharma), IL-7 (10 ng/ml) (Genzyme, Cambridge, Mass.), IL-1 (5 ng/ml), TNF (25 ng/ml) (Boehringer Mannheim, Indianapolis, Ind.), EPO (2 U/ml), KL (10 ng/ml) (R&D systems), FL (10 ng/ml) (purified after expression in Pichia pastoris from sequences published in Hannum et al. (1994) Nature 368:643. Cultures were incubated at 37° C. 5% $CO_2$ 95% air and medium was demi-depleted twice a week. Cultures were initiated with $CD34^+Lin^-CD10$ subsets ($CD10^+$ and $CD10^-$) and after 12 to 20 days, the cultured cells were stained with a direct two color method using fluorescein or PE-conjugated mAbs as shown in FIG. 12. Results in Table 9 are expressed as percentages of cells positive for the marker (after subtraction of background staining with an IgG1+IgG2a irrelevant control) and mean fluorescence intensity (mfi) of the positive cell population. Analysis was done applying an identical live (propidium iodide negative) or forward/scatter gate to cultures of $CD10^+$ and $CD10^-$ cells from the same experiment. In Table 9, N/A stands for not applicable and NT stands for not tested.

Figure 13A:
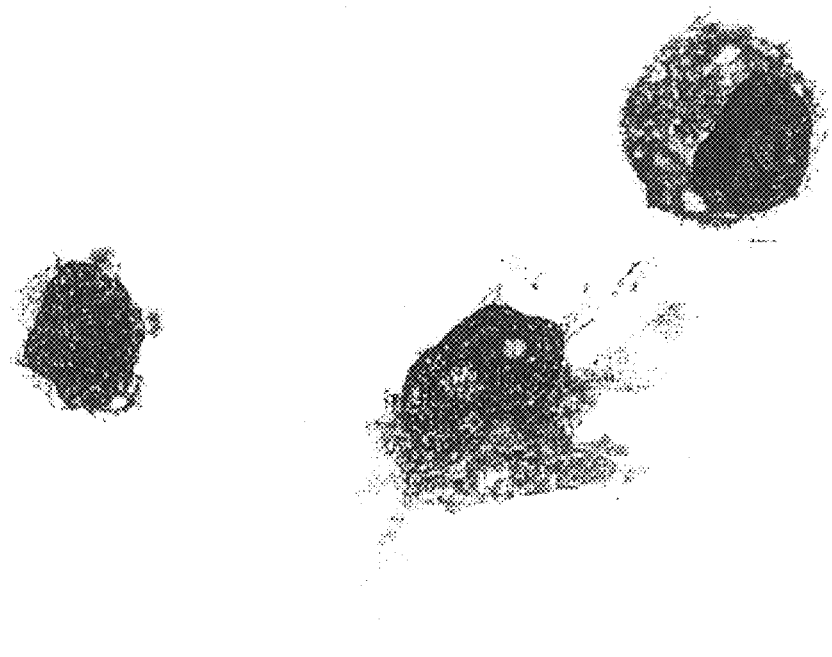
FIG. 13A : Photomicrograph (objective×100 oil) of cultured cells (day 12) deposited on slides by cytospin and stained with Wright-Giemsa.
Figure 13B:
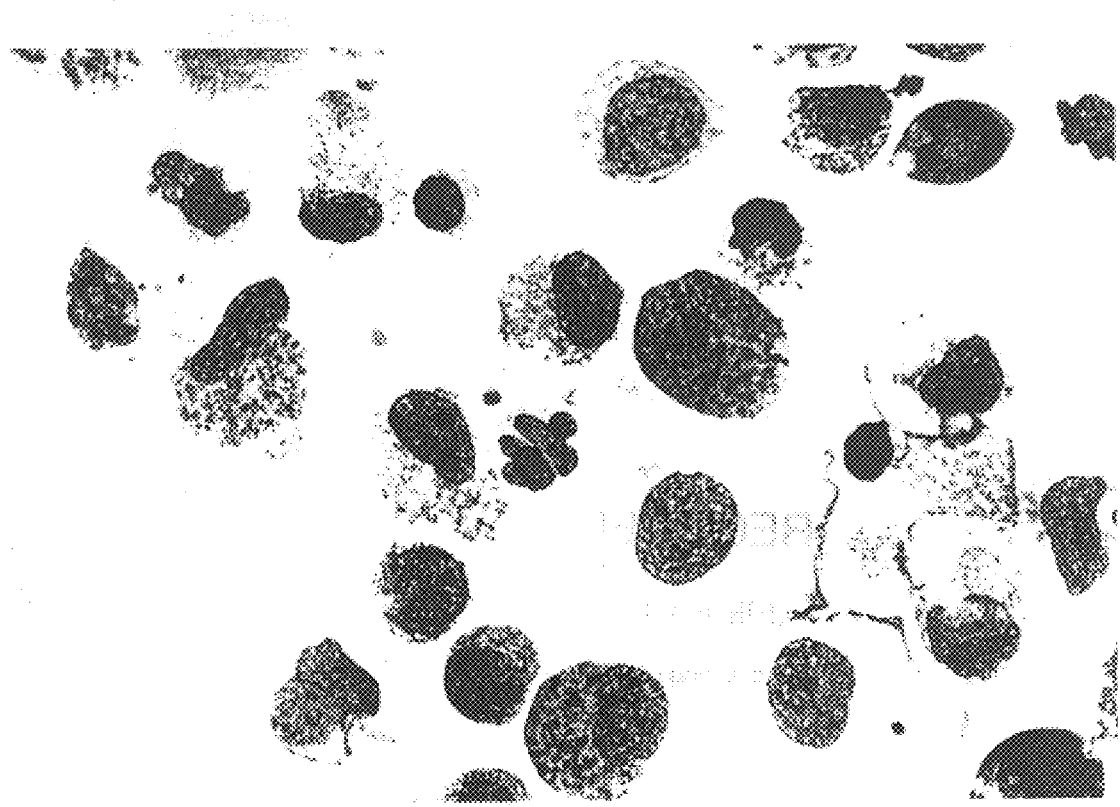
FIG. 13B depicts day 12 culture initiated with CD34$^+$Lin$^-$CD10$^-$ cells from the same ABM sample showing the presence of a wide variety of hematopoietic lineages.

In these cultures, $CD34^+Lin^-CD10^+$ cells grew modestly (total cellular expansion was 5 to 10 times less than cultures initiated with $CD34^+Lin^-CD10^-$ cells) and in all cases differentiated exclusively into cells with the morphological (FIG. 13-A) and immunophenotypic features (FIG. 12-A-B-C-D and Table 9) associated with dendritic cells (EC). Steinman (1991) Ann. Rev. Immunol. 9:271. 10⁺ cultures contained cells with very high forward and side scatter characteristics (FIG. 12-A), 40 to 63% of cells expressed very high levels of HLA-DR, 23 to 42% cells had bright expression of CD1a, 18 to 26% of the cells showed low levels of CD15, while none expressed the monocyte antigen CD14. The variability in size and CD1a expression are consistent with microheterogeneity within DC populations. Steinman (1991).

Under identical experimental conditions, $CD34^+Lin^-CD10^-$ cells grew strongly (60 to 95 fold cellular expansion in 12 to 15 days) and differentiated into a morphologically heterogeneous mixture of myelocytes, granulocytes, monocytes, macrophages, erythroblasts, DC and mast cells (FIG. 13-B) with diverse scatter characteristics (FIG. 12-E). These observations confirm that the culture conditions supported differentiation into a broad array of cells belonging to multiple hematopoietic lineages. Immunophenotypic analysis of $CD34^+Lin^-CD10^-$ cultures revealed 19 to 24% cells expressing high levels of CD14, 20 to 30% cells having CD15, 27 to 51% cells expressing HLA-DR albeit at lower levels than on cells in cultures of $CD34^+Lin^-CD10^+$ cells, and very few (0 to 2%) cells expressing CD1a.

EXAMPLE 9

Differentiation of cell populations into the megakaryocytic lineage was evaluated by establishing a liquid culture supplemented with Mpl-ligand/thrombopoietin and IL-3, both potent inducers of megakaryocyte development. Kaushansky et al. (1994) Nature 369:568. ABM $CD34^+Lin^-CD10$ ($CD10^+$ and $CD10^-$) cell subsets were cultured for 7 days in the presence of purified human recombinant IL3 (10 ng/ml) and 10% supernatant fluid of Cos-7 cells transfected with Mpl-ligand cDNA sequences, obtained from Bartley et al. (1994) Cell 77:1117, in IMDM with 5% human plasma. Medium was changed twice in 7 days. Under these culture conditions, most $CD34^+Lin^-CD10^+$ cells did not survive (16% viability with trypan blue exclusion) whereas the $CD10^-$ counterparts (98% viable) differentiated into megakaryoblasts.

Taken together, the data show that $CD34^+Lin^-CD10^+$ cells are not capable of generating erythroid, monocytic, granulocytic and megakaryocytic cells, but can differentiate into DC and all classes of lymphoid cells.

I claim:

1. A method of reconstituting the lymphoid cells of a subject comprising administering to the subject a therapeutically effective amount of an enriched population of human hematopoietic progenitor cells capable of differentiating into lymphoid cells and which do not differentiate into erythroid and myeloid cells, wherein at least 80% of the cells in the population express the markers CD34, CD45RA, CD10, but do not express CD2, CD3, CD4, CD8, CD19, CD20, CD 14, CD15, CD16, CD56 and glycophorin.

2. The method of claim 1 wherein at least 90% of the cells in the population express the markers CD34, CD45RA, CD10, but do not express CD2, CD3, CD4, CD8, CD19, CD20, CD14, CD15, CD16, CD56 and glycophorin.

3. The method of claim 1 wherein greater than 95% of the cells in the population express the markers CD34, CD45RA, CD10, but do not express CD2, CD3, CD4, CD8, CD19, CD20, CD14, CD15, CD16, CD56 and glycophorin.

4. A method of reconstituting the dendritic cells of a subject comprising administering to the subject a therapeutically effective amount of an enriched population of human hematopoietic progenitor cells capable of differentiating into dendritic cells and which do not differentiate into erythroid and myeloid cells, wherein at least 80% of the cells in the population express the markers CD34, CD45RA, CD10, but do not express CD2, CD3, CD4, CD8, CD 19, CD20, CD14, CD15, CD16, CD56 and glycophorin.

5. The method of claim 4 wherein at least 90% of the cells in the population express the markers CD34, CD45RA, CD10, but do not express CD2, CD3, CD4, CD8, CD19, CD20, CD14, CD15, CD16, CD56 and glycophorin.

6. The method of claim 4 wherein greater than 95% of the cells in the population express the markers CD34, CD45RA, CD 10, but do not express CD2, CD3, CD4, CD8, CD19, CD20, CD14, CD15, CD16, CD56 and glycophorin.

* * * * *